(12) United States Patent
Kumar et al.

(10) Patent No.: US 10,365,263 B1
(45) Date of Patent: Jul. 30, 2019

(54) PREDICTION OF CRUDE OIL BLEND COMPATIBILITY AND BLEND OPTIMIZATION FOR INCREASING HEAVY OIL PROCESSING

(71) Applicants: BHARAT PETROLEUM CORPORATION LIMITED, Mumbai (IN); INDIAN INSTITUTE OF TECHNOLOGY, DELHI, New Delhi (IN)

(72) Inventors: Rajeev Kumar, Mumbai (IN); Ravi Kumar Voolapalli, Mumbai (IN); Pranab Kumar Rakshit, Mumbai (IN); Sanjay Bhargava, Mumbai (IN); Sreedevi Upadhyayula, New Delhi (IN)

(73) Assignees: Indian Institute of Technology, Delhi, Delhi (IN); Bharat Petroleum Corporation Limited, Mumbai (IN)

( * ) Notice: Subject to any disclaimer, the term of this patent is extended or adjusted under 35 U.S.C. 154(b) by 0 days.

(21) Appl. No.: 15/937,397

(22) Filed: Mar. 27, 2018

(30) Foreign Application Priority Data

Jan. 29, 2018 (IN) .............................. 201821003341

(51) Int. Cl.
*G01N 33/28* (2006.01)
*C10G 7/12* (2006.01)

(52) U.S. Cl.
CPC .......... *G01N 33/2823* (2013.01); *C10G 7/12* (2013.01); *G01N 33/287* (2013.01);
(Continued)

(58) Field of Classification Search
CPC ..... G01N 33/2823; G01N 33/287; C10G 7/12
See application file for complete search history.

(56) References Cited

U.S. PATENT DOCUMENTS 5,699,269 A 12/1997 Ashe et al.
9,846,147 B2 12/2017 Kumar et al.
(Continued)

FOREIGN PATENT DOCUMENTS

EP 2 426 153 A1 2/2012

OTHER PUBLICATIONS

Asomaning et al., "Petroleum Stability and Heteroatom Species Effects in Fouling of Heat Exchangers by Asphaltenes," *Heat Transfer Engineering* 21(3):10-16, 2000. (8 pages).
(Continued)

*Primary Examiner* — John Fitzgerald
(74) *Attorney, Agent, or Firm* — Seed IP Law Group LLP

(57) ABSTRACT

Methods and systems for predicting crude oil blend compatibility and optimizing blends for increasing heavy crude oil processing are described. The method includes receiving ratios of physical parameters of crude oils for optimization of crude oil blend. The physical parameter ratios are based on Kinematic Viscosity (V), Sulphur (S), Carbon Residue (C), and American Petroleum Institute (API) gravity. The crude oil blend compatibility (K model) is determined and generated using the physical parameter ratios. The K model is developed by coefficients obtained by regression analysis between the ratios of physical parameters of known crude oils and composite compatibility measure determined from multiple compatibility test results of the known crude oils. The predicted crude oil blend compatibility can be used for optimizing heavy crude oil processing.

22 Claims, 14 Drawing Sheets

(52) U.S. Cl.
CPC . *C10G 2300/202* (2013.01); *C10G 2300/302* (2013.01); *C10G 2300/308* (2013.01)

(56) References Cited

U.S. PATENT DOCUMENTS

| | | |
|---|---|---|
| 2010/0174494 A1 | 7/2010 | De Peinder et al. |
| 2016/0195506 A1 | 7/2016 | Kumar et al. |
| 2017/0322131 A1 | 11/2017 | Kumar et al. |

OTHER PUBLICATIONS

Asomaning, "Test Methods for Determining Asphaltene Stability in Crude Oils," *Petroleum Science and Technology* 21(3 &4):581-590, 2003. (11 pages).

ASTM International, "Standard Test Method for Cleanliness and Compatibility of Residual Fuels by Spot Test," Designation: D4740-04, Originally approved 1992, Current edition approved May 1, 2014, 3 pages.

Centeno et al., "Testing various mixing rules for calculation of viscosity of petroleum blends," *Fuel* 90:3561-3570, 2011.

Hong et al. "Precipitation and Fouling in Heavy Oil-Diluent Blends," *Heat Exchanger Fouling and Cleaning VII RP5*:23-31, 2007.

Gabrienko et al., "Effect of Temperature and Composition on the Stability of Crude Oil Blends Studied with Chemical Imaging in Situ," *Energy Fuels* 29:7114-7123, 2015.

Goual et al., "Measuring Asphaltenes and Resins, and Dipole Moment in Petroleum Fluids," *AIChE Journal* 48(11):2646-2663, 2002.

Guzmán et al., "Methods for determining asphaltene stability in crude oils," *Fuel* 188:530-543, 2017.

Hamza et al., "Blending Effects on Crude Oil Stability: An Experimental Study," *19th International Conference on Chemical and Molecular Engineering*, Paris, France, Apr. 18-19, 2017, p. 1681. (Abstract).

Kumar et al., "Improve feedstock selection for your refinery," *Hydrocarbon Processing*:65-71, 2012.

Luo et al., "Effects of asphaltene content on the heavy oil viscosity at different temperatures," *Fuel* 86:1069-1078, 2007.

Mahmoud et al., "Compatibility Assessment of Crude Oil Blends Using Different Methods," *Chemical Engineering Transactions* 57:1705-1710, 2017.

Mansoori, "Modeling of asphaltene and other heavy organic depositions," *Journal of Petroleum Science & Engineering* 17:101-111, 1997.

Mendoza de la Cruz et al., "Incompatibility Determination of Crude Oil Blends from Experimental Viscosity and Density Data," *Energy Fuels* 29:480-487, 2015.

Nazar et al., "Investigation of Asphaltene Stability in the Iranian Crude Oils," *Iranian Journal of Chemical Engineering* 5(1):3-12, 2008.

Parihar et al., "Optimize hydrogen management for distillate production," *Hydrocarbon Processing*:61-65, 2012.

Rana et al., "A review of recent advances on process technologies for upgrading of heavy oils and residua," *Fuel* 86:1216-1231, 2007.

Rathore et al., "Assessment of crude oil blends: a refiner's assessment of the compatibility of opportunity crudes in blends aims to avoid the processing problems introduced by lower-quality feedstocks," Oct. 2011, URL= http://www.digitalrefining.com/article_1000381.pdf, 6 pages.

Rodríguez et al., "Experimental Setups for Studying the Compatibility of Crude Oil Blends under Dynamic Conditions," *Energy Fuels* 30:8216-8225, 2016.

Rogel et al., "Density Estimation of Asphaltenes Using Molecular Dynamics Simulations," *Energy & Fuels* 17:378-386, 2003.

Schermer et al., "Simple Techniques for Evaluation of Crude Oil Compatibility," *Petroleum Science and Technology* 22(7 & 8):1045-1054, 2004. (12 ppages).

Stratiev et al., "Investigation of relations between properties of vacuum residual oils from different origin, and of their deasphalted and asphaltene fractions," *Fuel* 170:115-129, 2016.

Stratiev et al., "Investigation of Relationships between Petroleum Properties and Their Impact on Crude Oil Compatibility," *Energy Fuels* 29:7836-7854, 2015.

Trejo et al., "Thermogravimetric determination of coke from asphaltenes, resins and sediments and coking kinetics of heavy crude asphaltenes," *Catalysis Today* 150:272-278, 2010.

Wiehe et al., "The Oil Compatibility Model and Crude Oil Incompatibility," *Energy & Fuels* 14:56-59, 2000.

PREDICTION OF CRUDE OIL BLEND COMPATIBILITY AND BLEND OPTIMIZATION FOR INCREASING HEAVY OIL PROCESSING

TECHNICAL FIELD

The present invention relates to predicting crude oil blend compatibility and, in particular, relates to predicting compatibility of crude oils and their blends based on physical parameter ratios of the crude oils to increase heavy oil processing in refineries.

BACKGROUND

Refineries typically process a blend of crude oils rather than a single crude oil to ensure that an optimum product mix as required by markets, which varies from time to time, can be obtained at minimum costs. Increasingly, refineries are looking for ways to co-process heavy crude oils with light crude oils. Heavy crude oils have a high amount of paraffin or asphaltene or both. When there is a high paraffin content, it results in high viscosity and high pour point making transportation difficult. On the other hand, a high asphaltene content causes precipitation, flocculation, instability, and incompatibility related problems during processing. Therefore, increasing co-processing of heavy oil components is a real challenge.

To increase the heavy oil content in the mix of crude oils processed and also for suitable oil selection for processing, refiners encounter five common problems on day-to-day operation viz. (i) Incompatibility/Stability issues when the crude oils are blended, (ii) high viscosity of the blend, (iii) high pour point of the blend, (iv) high sulphur content in the blend, and (v) high vacuum residue yields upon processing. While selection of crude oils and blends is done, various simulations and correlations are used to ensure viscosity, pour point, distillation and residue yields, and sulphur content is appropriately managed. However, incompatibility of crude oils and blends is still a grey area, which is currently being managed by previous operational experience and compatibility test results received from oil testing laboratories. Incompatibility is a serious problem which causes asphaltene precipitation and severely affects various equipment viz. tanks, heat exchangers, separators, columns pumps, etc., and in the absence of viable models to manage incompatibility, refining operations and costs can get severely affected.

There are various test methods reported and being practiced at laboratories in order to study the stability of crude oils and blends viz. colloidal instability index (CII), colloidal stability index (CSI), Stankiewicz plot (SP), qualitative-quantitative analysis (QQA), stability cross plot (SCP), Heithaus parameter (or parameter P), Heptane Dilution (HD), toluene equivalence (TE), spot test and oil compatibility model (OCM). Some of the tests are correlation based, which requires Saturates, Aromatics, Resins and Asphaltene (SARA) analysis data to predict the stability of crude oils. OCM, TE and P parameter methods require asphaltene precipitation data when solvents like heptane or toluene are added in different ratio to estimate the stability of crude oils. Thus, these tests require samples of the crude oils and blends to be chemically tested in the laboratory before a decision can be made for purchasing and processing the crude oils. Moreover, as the test results may vary depending on the test method used, methods based on one or two tests are incapable of accurately predicting compatibility. In addition to this, models reported in the literature are not applicable to crude oils which have a low amount of asphaltene (≤0.5 wt %) and high amount of saturates. As a result, more than three to four tests are needed to confirm the compatibility of crude oils and blends. While these methods are comprehensive, they are experiment based and time consuming. By the time results are available, suboptimal crude oil blends are processed or asphaltene precipitation problems are created in the refineries, which requires substantial efforts and price to resolve.

In the past, various research groups have attempted to develop methods and correlation models to predict asphaltene precipitation and crude oil stability and compatibility. Insolubility number (IN) and solubility blending number (SBN) have been recognized as important parameters to predict asphaltene precipitation Higher the SBN number, there is less possibility for incompatibility. Sollaimany and Bayandori studied the asphaltene deposition behavior. According to their results, CSI such as the (Aromatics+Resin)/(Asphaltene+Saturates) ratio and (Aromatics+Resin)/Asphaltene ratio are less significant for asphaltene stability rather structural parameters of asphaltenes and resins are important. Asomaning conducted various tests such as spot test, CII, Asphaltene/Resin ratio, and solvent method with near-infrared spectroscopy to predict the asphaltene stability in crude oils. CII and solvent titration method prediction results found closer to the field deposition results. However, some of the papers concluded that CII is not an appropriate method for prediction of asphaltene precipitation when asphaltene content is low and saturate content is high. Guzman R., et. al., have extensively reviewed different methods and concluded that CII and SP methods were predicts unsatisfactory results, on the other hand, QQA and SCP predicts better for asphaltene stability in crude oils. Stratiev et al. have correlated asphaltene solubility with the asphaltene hydrogen content and the oil solubility power correlated well with the oil saturate content. Higher asphaltene aromaticity help in solubilizing asphaltene compounds. They also found that some of the physical parameters such as specific gravity, Conradson carbon, and viscosity are able to predict the hydrogen, saturates, and asphaltenes content of vacuum residual oils. Similarly, there are few tests reported to predict asphaltene precipitation based on experimental physical properties data. Jose et. al., predicted incompatibility of blends of crude oils with liquid hydrocarbon from dynamic viscosity and density. They observed that increase in viscosity and density of the crude oil blends mixed with liquid hydrocarbon increases tendency of asphaltene aggregation. Incompatible region determined by viscosity data is more superior to density data. Thus, while there are multiple different approaches studied for determining compatibility of crude oils in blends, the methods are usually time consuming and not fully reliable.

SUMMARY

This summary is provided to introduce concepts related to prediction of compatibility of crude oils and blends, which is further described below in the detailed description. This summary is not intended to identify essential features of the claimed subject matter nor is it intended for use in determining or limiting the scope of the claimed subject matter.

Methods and systems for predicting crude oil blend compatibility and optimizing crude oil blend for increasing heavy oil processing are described. In one aspect, a method for predicting crude oil blend compatibility includes receiving ratios of physical parameters of crude oils for optimization of crude oil blend. The physical parameter ratios of the crude oil are based on Kinematic Viscosity (V), Sulphur (S), Carbon Residue (C), and American Petroleum Institute (API) gravity. In one example, the physical parameter ratios include Log (Sulphur (S))/Carbon Residue (C), API/Sulphur, and Kinematic Viscosity (V)/C. The crude oil blend compatibility (K model) is determined and generated using the physical parameter ratios. The K model is developed by coefficients obtained by regression analysis between the ratios of physical parameters of crude oils and composite compatibility measure obtained from multiple compatibility test results of the crude oil and blends. Further, optimized blends can be determined based on the K model and additional constraints for increasing heavy crude oil processing without facing any operational issues related to crude oil blend compatibility in refineries.

BRIEF DESCRIPTION OF DRAWINGS

The detailed description is provided with reference to the accompanying figures. In the figures, the left-most digit(s) of a reference number identifies the figure in which the reference number first appears. The same numbers are used throughout the drawings to reference like features and components.

DETAILED DESCRIPTION

Figure 1:
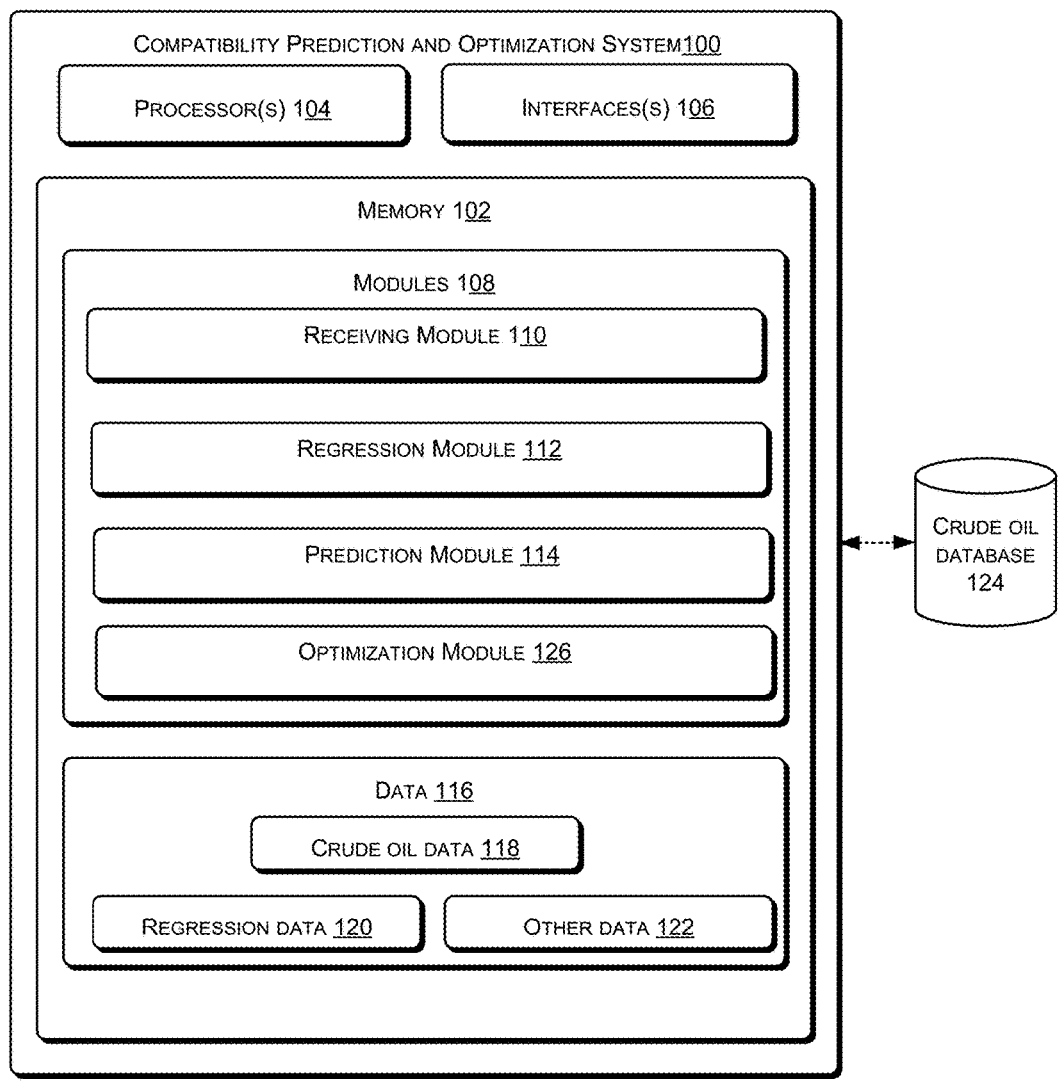
FIG. 1 illustrates a system for prediction of compatibility of crude oils for blending, in accordance with an example implementation of the present subject matter.

The present subject matter provides for quick and effective methods, systems, and apparatuses for prediction of crude oil blend compatibility and blend optimization of crude oils for increasing heavy oil processing. The prediction model is based on the measurement of a few bulk physical parameters ratio, which are conventionally and regularly analyzed at quality control laboratory of refineries. Hence, additional tests are not required to be done and the blending decisions can be made quickly. In contrast to conventional methods, the present subject matter does not require comprehensive laboratory testing for compatibility checking and blending, which otherwise normally takes about two weeks' time. Furthermore, using existing laboratory test methods, blends of only two crude oils can be optimized at a time. To optimize a blend of three crude oils, first a compatible blend of two crude oils has to be obtained and then a mix of the two crude oils with the third has to be optimized. If additional crude oils are to be blended, the compatibility checking and blend optimization become even more complicated. However, the present subject matter allows for compatibility prediction and optimization of blends having n-crude oils based on the physical parameter ratios of each of the n-crude oils. Thus, the present subject matter can be used for increasing heavy oil processing and helps to substantially eliminate operational problems caused due to crude oil blend incompatibility in refineries.

For convenience, before further description of the present subject matter, certain terms employed in the specification and examples are explained here. These explanations should be read in the light of the remainder of the disclosure and understood as by a person of skill in the art. The terms used herein have the meanings recognized and known to those of skill in the art, however, for convenience and completeness, particular terms and their meanings are set forth below.

The term crude oil as used herein includes crude oil blends as well. Hence, a crude oil that is being blended with other crude oils may itself be a blend of two or more crude oils.

Heavy crude oil (Heavy oil) and Light crude oil (Light oil) are the two major categories of crude oil that are generally used in refineries, as will be understood by a person skilled in the art. Heavy crude oil generally refers to a crude oil having inferior physico-chemical properties such as low API, high viscosity, high pour point, high vacuum residue content with high impurities like metals, asphaltenes, nitrogen etc. Further, a heavy crude oil may be asphaltenic or non-asphaltenic. Light crude oil generally refers to a crude oil having high API, low sulphur, low viscosity, low pour point and with less impurities.

A fraction of a crude oil refers to a group of hydrocarbon constituents of the crude oil that have a boiling point in a particular range and are hence obtained as a single fraction during distillation of the crude oil. For example, Naphtha, kerosene, diesel, petrol, vacuum gas oil, long residue, vacuum residue etc. are different fractions of crude oils. Typically, the hydrocarbon constituents of a fraction are highly miscible among themselves and difficult to separate. Generally, higher boiling fractions have a lower commercial value than lower boiling fractions. Furthermore, a heavy oil generally has greater amounts of higher boiling fractions than a light oil. Hence, typically heavy oils have less commercial value than light oils.

The term compatibility when used in the context of a blend of crude oils refers to the likelihood of one or more fractions separating out from the blend of crude oils due to precipitation. Hence, when a blend is compatible, it means that none of the fractions in the blend are likely to precipitate out and the blend can be processed as a single homogeneous fluid. When a blend is incompatible, it means that precipitation is likely to happen and hence the blend is not suitable for refinery operations as it will adversely affect refining equipment during processing. The precipitation is typically due to asphaltenes separating out from the oil.

The term compatibility when used in the context of a single crude oil refers to stability. The term stability as used herein refers to the potential of a crude oil to cause a blend to become incompatible when the crude oil is blended with a crude oil of a different category. For example, it is generally known that when a heavy oil is mixed with a heavy oil or when a light oil is mixed with a light oil, there are no issues of precipitation or incompatibility. However, when a heavy oil is mixed with a light oil or vice-versa, the blend can become incompatible. Stability of a crude oil thus indicates whether the crude oil can lead to an incompatible blend when mixed with another crude oil of a different category. Stable crude oils do not lead to incompatible blends, whereas unstable crude oils typically lead to incompatible blends unless the blend composition is carefully controlled. The term metastable is also used sometimes to refer to crude oils that are not definitely stable or unstable.

Since crude oils are themselves blends of various fractions, the term self-incompatibility is sometimes used to refer to a crude oil whose fractions are not compatible between themselves and hence a self-incompatible crude oil can result in precipitation of one or more fractions even without being mixed with another crude oil.

The term known crude oil or known crude oil sample refers to a crude oil or sample that has been characterized by physical and chemical techniques. The term unknown crude oil or unknown crude oil sample refers to a crude oil or sample that has not been characterized by chemical techniques.

Various other terms related to components of a crude oil, such as saturates, aromatics, resin, etc., and terms related to properties of a crude oil, such as API gravity, carbon content, viscosity, pour point, etc., are used herein. Such terms will be well understood by a person skilled in the art and are not separately defined.

In the drawings, tables, and description, for sake of representation and ease of discussion, certain symbols are used, which may represent different terms in different contexts. For example, in the context of techniques that use Saturates, Aromatics, Resin, and Asphaltene (SARA) measurements, S may indicate Saturates, Ar may indicate Aromatics, A may indicate Asphaltenes, and R may indicate resin. However, in the context of physical parameters, S may indicate Sulphur, A may indicate API Gravity, C may indicate Carbon Residue, such as Conradson Carbon residue (CCR), and V may indicate Kinematic Viscosity. Hence, the symbols are to be understood based on the context in which they are used.

In one implementation, a method for predicting a crude oil blend compatibility of unknown crude oils includes receiving values for a plurality of physical parameter ratios of samples of the crude oils to be blended. The plurality of physical parameter ratios includes ratios based at least on sulphur, carbon residue, kinematic viscosity, and API gravity. For example, the plurality of physical parameter ratios may include Log (Sulphur)/Carbon Residue ratio, Kinematic Viscosity/Carbon Residue ratio, and API Gravity (API)/Sulphur (S) ratio. In one example, the carbon residue may be determined as Conradson Carbon Residue (CCR). The crude oil blend compatibility can be then determined based on a prediction model by using the received values as an input to the prediction model. In one example, the prediction model is based on coefficients of regression obtained from correlating the individual and/or composite decision of multiple different compatibility test results with the plurality of physical parameter ratios for known crude oils and blends. The crude oil blend compatibility predicted using samples of unknown oils, including heavy oils, can be used to determine a composition of a crude oil blend, composed of the unknown oils, that can be used for increasing heavy oil processing while meeting various requirements of yield, viscosity, compatibility, etc.

In one implementation, the prediction model for crude oil blend compatibility is generated based on the measurement of a few physical parameter ratios. For this, in one example, a detailed investigation of relationships between different physical parameters ratios, such as API/sulphur, sulphur/viscosity, carbon/API, carbon/sulphur, viscosity/API, viscosity/carbon, and crude oil blend compatibility can be done. As used herein, carbon refers to carbon residue as measured by, for example, CCR or other carbon residue determination methods. It does not refer to elemental carbon content.

In one example, multiple different crude oil samples may be used for development of the prediction model. Different compatibility tests, such as CII, CSI, SP, QQA, SCP, spot test and oil compatibility model (OCM) can be conducted for each sample and average results can be considered for estimation of model coefficient parameters. Based on the impact of physical parameters ratio and average compatibility results, a mathematical model (K) can be generated to quickly predict the compatibility for unknown samples.

Prediction of spot test shades for identification of light and heavy oils may also be done in one aspect of the present subject matter.

Using the K model, optimal blends can be estimated for different crude oils and crude oil blends. The optimization of blend can include, in addition to compatibility, optimization of viscosity, pour point, and vacuum residue yields. This will be helpful to increase the heavy oil processing with no asphaltene precipitation or other adverse effects on the refining operations. Thus, the processing of compatible crude oils and/or blends as determined by the present subject matter may help in reducing the consumption of chemicals like antifoulant and may help avoid incompatibility related problems that cause fouling of equipment, piping, heat exchangers, tanks, etc., in refineries.

The above and other features, aspects, and advantages of the subject matter will be better explained with regard to the following description and accompanying figures.

FIG. 1 illustrates various components of a compatibility prediction and optimization system 100, according to an embodiment of the present subject matter. The compatibility prediction and optimization system 100 is also referred to as system 100 hereinafter. The system 100 includes one or more processor(s) 104, one or more interfaces 106 and a memory, such as a memory 102, coupled to the processor(s) 104. It will be understood that the system 100 may be implemented as any suitable computing system known in the art, such as a desktop, a laptop, a server, and the like.

The interfaces 106 may include a variety of software and hardware interfaces, for example, interfaces for peripheral device(s), such as a keyboard, a mouse, an external memory, and a printer. The interfaces 106 can facilitate multiple communications within a wide variety of networks and protocol types, including wired networks, for example, local area network (LAN), cable, etc., and wireless networks, such as Wireless LAN (WLAN), cellular, or satellite. For facilitating communications, the interfaces 106 may include one or more ports for connecting a number of devices to each other or to another computing system.

The processor 104 can be a single processing unit or a number of units, all of which could include multiple computing units. The processor 104 may be implemented as one or more microprocessors, microcomputers, microcontrollers, digital signal processors, central processing units, state machines, logic circuitries, and/or any devices that manipulate signals based on operational instructions. Among other capabilities, the processor 104 is configured to fetch and execute computer-readable instructions and data stored in the memory 102.

The functions of the various elements shown in the figures, including any functional blocks labelled as "processor(s)", may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" should not be construed to refer exclusively to hardware capable of executing software, and may implicitly include, without limitation, digital signal processor (DSP) hardware, network processor, application specific integrated circuit (ASIC), field programmable gate array (FPGA), read only memory (ROM), random access memory (RAM), and non-volatile storage.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 102 includes module(s) 108 and data 116.

The modules 108, amongst other things, include routines, programs, objects, components, data structures, etc., which perform particular tasks or implement particular abstract data types. The modules 108 further include, for example, a receiving module 110, a regression module 112, a prediction module 114, and an optimization module 126.

The data 116 serves, amongst other things, as a repository for storing data processed, received and generated by one or more of the modules 108. The data 116 may include data related to samples of known crude oils stored as crude oil data 118, regression data 120 and other data 122. The data 116 also includes data generated as a result of the execution of one or more modules.

In operation and to generate a compatibility prediction model, according to an implementation of the present subject matter, the receiving module 110 of the system 100 receives physical properties of various crude oils for a plurality of known crude oil samples. The physical properties can include, for example, one or more of Density, Specific Gravity and/or American Petroleum Institute (API) Gravity, Sulphur, Mercaptan, Kinematic Viscosity (V), Pour Point, ASTM Distillation, Freezing Point, Carbon residue measured as Conradson Carbon Residue (CCR) or Micro Carbon Residue (MCR) or Ramsbottom Carbon Residue (RCR), and the like. These properties may be determined by any industrial protocol methods as known in the art, for example, ASTM methods. It will be understood that properties that can be determined by simple lab tests without requiring chemical analysis are referred to as physical properties though it may include estimates of chemical constituents, such as sulphur or carbon residue. These lab tests are simpler, easier, and faster than chemical analysis based tests that are typically required to determine the chemical composition of crude oils.

In one example, the receiving module 110 also receives information regarding chemical composition of the known crude oil samples including at least SARA content, i.e., Saturates, Aromatics, Resin, and Asphaltenes content of each known crude oil sample for generating the compatibility prediction model.

The physical property data and the chemical composition data may be stored in a crude oil database 124 for further use in the generation of the compatibility prediction model, interchangeably referred to as compatibility model or K model. The regression module 112 processes this data for calculation of regression coefficients for the compatibility prediction model that can be used to predict the compatibility of crude oil blends for unknown crude oils. The crude oil database 124 may also be used to store the computed coefficients of regression for plurality of known crude oil samples and their measured physical properties. Thus, it will be understood that the crude oil database 124 may be used for storing any relevant data relating to the system 100.

Though the K model is referred to as compatibility model, it will be understood that when used for a single crude oil the K model indicates the stability of the crude oil and when used for a blend of crude oils, it indicates the compatibility of the blend. Thus, a single model can be used for both stability and compatibility prediction.

In one implementation, the regression module 112 determines parameter ratios based on API gravity (referred to as API or A), Sulphur (S), Kinematic Viscosity (V), and carbon residue content (C). In one example, the parameter ratios are selected from API/S, S/V, C/API, C/S, 1/C, log (S)/C, V/API, and V/C based on the impact of the parameter ratio on the compatibility. The parameter ratios may be selected such that the four parameters, API, S, V, and C are accounted for in one or more of the selected parameter ratios. In one example, the parameter ratios include at least log (S)/C, A/S, and V/C.

Further, the regression module 112 determines a composite compatibility measure for each known crude oil sample using a plurality of compatibility tests known in the art. In one example, at least six methods known in the art selected from CII, CSI, SI, SP, QQA, SCP, spot test, Heithaus parameter, and oil compatibility model (OCM) are used. The composite compatibility measure can be an average of the values of the compatibility measures or any other mathematical combination of the values of the compatibility measures. For example, a weight may be given to the compatibility value obtained from each method based on relative accuracy of the method and the composite compatibility measure may be a weighted average of the values. Other ways of mathematically combining the values to derive the composite compatibility measure may also be used. The composite compatibility measure corresponds to the compatibility parameter K. The regression module 112 can then compute coefficients and generate a mathematical model to determine value of the compatibility parameter K based on the values of the physical parameter ratios. In one implementation, the calculation of the coefficients of regression is based on a method of linear regression. However, it will be understood that other methods of non-linear regression, such as polynomial regression and logarithmic regression, may also be used for determination of the regression coefficients.

The mathematical model to determine the compatibility parameter K based on the parameter ratios is called the compatibility prediction model and is also referred to as the K model. In one example, the K model is given by equation 1 below:

$$K = k1*\left(\frac{1}{C}\right) + k2*\left(\frac{C}{A}\right) + k3 + *\left(\frac{C}{S}\right) + \quad \text{(Eq. 1)}$$
$$k4*\left(\frac{\log(S)}{C}\right) + k5*\left(\frac{A}{S}\right) + k6*\left(\frac{S}{V}\right) + k7*\left(\frac{V}{A}\right) + k8*\left(\frac{V}{C}\right)$$

where k1, k2 . . . k8 are the coefficients of regression.

In one example, if certain parameter ratios are not used in the modelling then their respective coefficients can be considered to be zero.

Further, the prediction module 114 can predict the compatibility of unknown crude oil blends based on the coefficients of regression and prediction model generated by the regression module 112. Also, based on the predicted compatibility, an optimized blend can be determined by the optimization module 126 and further decisions can be taken, for example, regarding crude oils to be purchased, efficient resource utilization in the refinery, and the like.

For determination of the optimized blend, the optimization module 126 can implement a multi-objective non-linear optimization model. As discussed above, in addition to compatibility, certain other parameters, such as viscosity and pour point have to be optimized so that transportation and refining of the crude oil blend can be performed without fouling or coking. Further, the yields of high commercial value products need to be maximized for profitability of the refining operations. Furthermore, since the objective is to increase processing of heavy oils in combination with other oils, the optimization can be performed for blends whose compatibility parameter K is greater than or equal to zero. In one example, the constraints or objectives for the multi-objective non-linear optimization model implemented by the optimization module 126 can be represented as:

Kinematic Viscosity @ 40° C. of blend, V≤10 cSt
Vacuum Residue (VR) Yield of blend, Y≤20 wt %
Pour Point of blend, P≤0° C.
Sulphur in blend, S≤2.5 wt %
Compatibility parameter of blend, K>=0

It will be understood that the above-mentioned constraints values can be varied depending upon the refinery configuration and requirements by the product planning and scheduler departments. For example, a refinery that may be able to handle more viscous crude oil blends may use V≤20 cSt as a constraint instead of V≤10 cSt.

Based on the constraints, a blend of n crude oils $CO_1$, $CO_2$, . . . $CO_n$ can be optimized so that the sum of their respective weight ratios $x_1$, $x_2$, . . . $x_n$ in the blend equals 1. i.e., $x_1+x_2+ \ldots x_n=1$ Here the acronym CO refers to Crude Oil and $CO_1$, $CO_2$, . . . $CO_n$ refer to the 'n' crude oils. To ensure that there is a minimum percentage of each crude oil in the blend, additional constraints can be placed on the minimum value of each weight ratio. For example, a constraint can be placed that each of $x_1$, $x_2$, . . . $x_n$>=0.1. In another example, different constraints can be placed for weight ratios of different crude oils, such as $x_1$>=0.3 and $x_2$>=0.1.

In the above multi-objective model, the compatibility parameter K of the blend can be determined using the equation 1 as discussed above and the values of the parameters C, API, V, Y, P, and S for the blend can be determined from the corresponding values in the crude oils based on the weight ratios of the crude oils in the blend using various mathematical models known in the art as represented below:

C=function of $(x_1 C_{CO1}, x_2 C_{CO2}, \ldots x_n C_{COn})$
Where $C_{CO1}$, $C_{CO2}$, . . . $C_{COn}$ are the Carbon residues of $CO_1$, $CO_2$, . . . $CO_n$ respectively.

A=function of $(x_1 A_{CO1}, x_2 A_{CO2}, \ldots x_n A_{COn})$
Where $A_{CO1}$, $A_{CO2}$, . . . $A_{COn}$ are the API gravities of $CO_1$, $CO_2$, . . . $CO_n$ respectively.

V=function of $(x_1 V_{CO1}, x_2 V_{CO2}, \ldots x_n V_{COn})$
Where $V_{CO1}$, $V_{CO2}$, . . . $V_{COn}$ are the kinematic viscosities of $CO_1$, $CO_2$, . . . $CO_n$ respectively.

Y=function of $(x_1 Y_{CO1}, x_2 Y_{CO2}, \ldots x_n Y_{COn})$
Where $Y_{CO1}$, $Y_{CO2}$, . . . $Y_{COn}$ are the Vacuum Residue yields of $CO_1$, $CO_2$, . . . $CO_n$ respectively.

P=function of $(x_1 P_{CO1}, x_2 P_{CO2}, \ldots x_n P_{COn})$
Where $P_{CO1}$, $P_{CO2}$, . . . $P_{COn}$ are the pour points of $CO_1$, $CO_2$, . . . $CO_n$ respectively.

S=function of $(x_1 S_{CO1}, x_2 S_{CO2}, \ldots x_n S_{COn})$
Where $S_{CO1}$, $S_{CO2}$, . . . $S_{COn}$ are the sulphur contents in $CO_1$, $CO_2$, . . . $CO_n$ respectively.

Thus, the optimization module 126 can determine an optimized blend based on the compatibility parameter (K) model and multi-objective non-linear program model that can be processed in refineries easily. As can be seen from the optimization technique discussed above that an optimized blend of n-crude oils can be directly determined based on the techniques of the present subject matter in contrast to prior art methods that could optimize composition of two crude oils in a blend at a time.

In one example, the unknown crude oil may be a refinery product stream. The refinery product stream can include at least one of clarified oil, bitumen, vacuum residue, long residue, light cycle oil, heavy cycle oil, vacuum gas oil, kerosene, diesel, Gas oil, atmospheric residue, Fuel Oil, Low Sulphur Heavy Stock, unconverted oils, bottom residue and their unknown blends. Accordingly, the optimization module 126 can determine the optimized blend of the unknown crude oil with the one or more other crude oils. This can be used, for example, when hydrocarbon product streams are available in surplus in the running operation in refinery and for optimum use of the surplus stream, it can be blended with crude oils and diverted to crude distillation unit. In another example, the unknown crude oil can be a crude oil, synthetic crude oil, an unknown hydrocarbon mixture, and a combination thereof.

Figure 2:
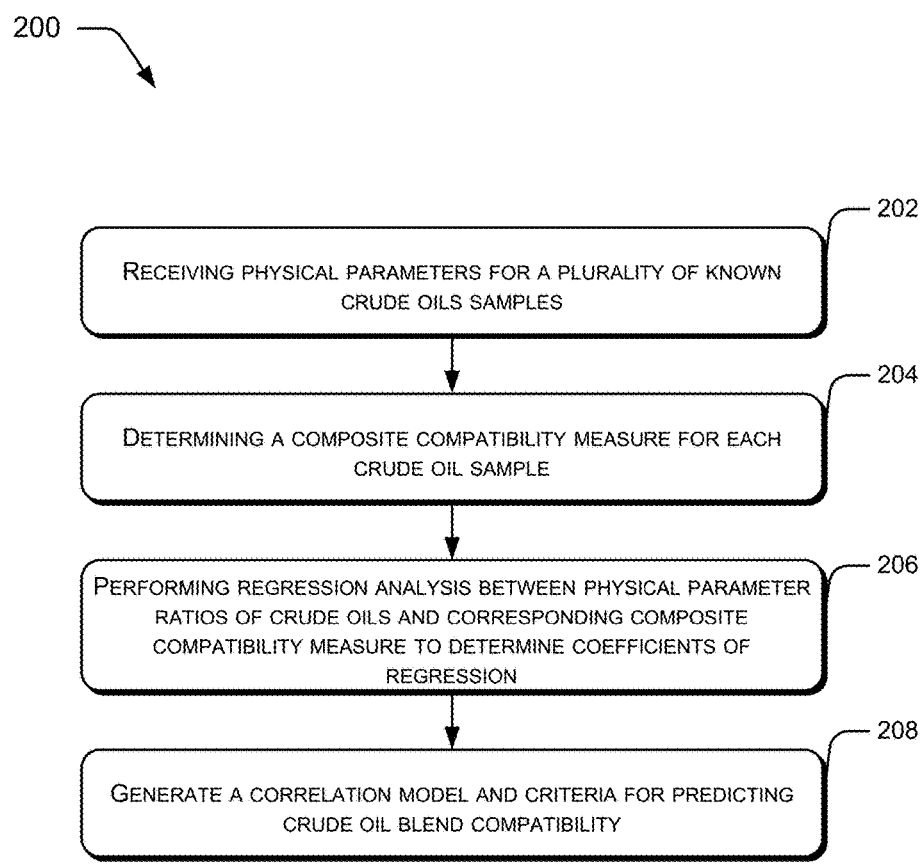
FIG. 2A illustrates a method of development of K model, in accordance with an example implementation of the present subject matter.
FIG. 2B illustrates a method of prediction of compatibility and optimization of blend using the K model, in accordance with an implementation of the present subject matter.
Figure 2B:
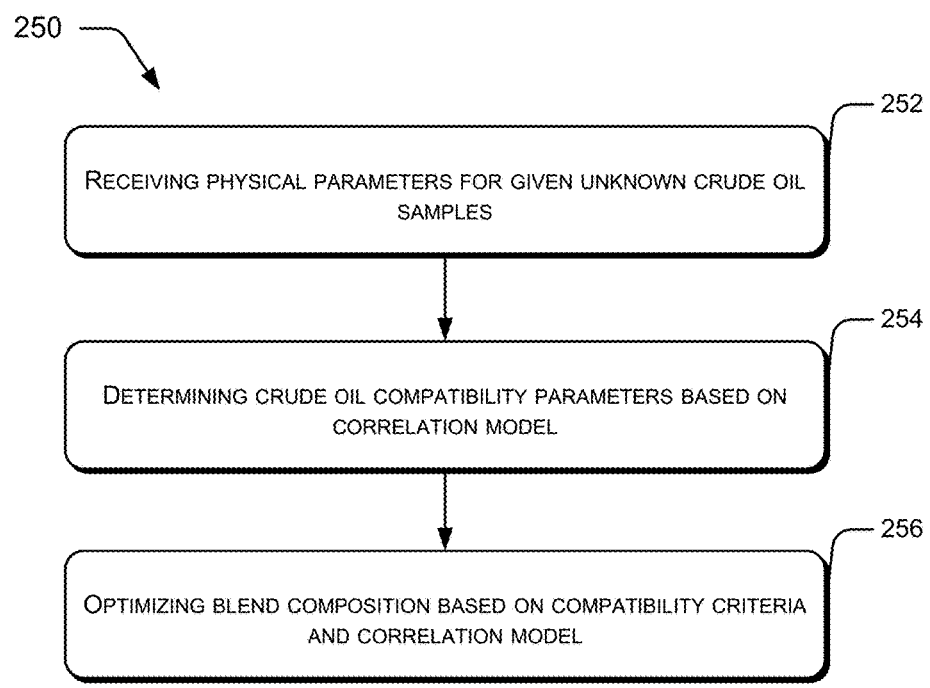

FIG. 2A illustrates an example method 200 for development of K model, in accordance with an example implementation of the present subject matter. FIG. 2B illustrates a method 250 of prediction of compatibility and optimization of blend using the K model, in accordance with an implementation of the present subject matter. For explanation, the steps of calculation of coefficients of regression, prediction of compatibility, and optimization of blend are described with reference to the system 100.

The example methods may be described in the general context of computer executable instructions. Generally, computer executable instructions can include routines, programs, objects, components, data structures, procedures, modules, functions, etc., that perform particular functions or implement particular abstract data types. The methods may also be practiced in a distributed computing environment where functions are performed by remote processing devices that are linked through a communications network. In a distributed computing environment, computer executable instructions may be located in both local and remote computer storage media, including memory storage devices.

The order in which the method blocks are described in methods 200 and 250 is not intended to be construed as a limitation, and any number of the described method blocks can be combined in any order to implement the method, or an alternative method. Additionally, individual blocks may be deleted from the methods without departing from the spirit and scope of the subject matter described herein. Furthermore, the methods can be implemented in any suitable hardware, software, firmware, or combination thereof.

Referring to method 200 illustrated in FIG. 2A, at block 202, physical parameter values and chemical composition information for a plurality of known crude oils samples are received. The physical parameters include at least API gravity, Sulphur, Viscosity, and Carbon content. Based on these physical parameters, various physical parameter ratios can be estimated. In one example, at least Log (S)/C, A/S, and V/C are estimated. The chemical composition information includes Saturates, Aromatics, Asphaltenes, and Resin content and is used to generate the compatibility model. For example, the physical parameter values and chemical composition information may be received by the receiving module 110.

At block 204, a composite compatibility measure for each known crude oil sample is determined. For this, compatibility tests are conducted based on a plurality of, for e.g., at least six, known prior art compatibility tests and a composite measure is obtained based on an average result of the prior art compatibility tests. For example, the composite compatibility measure may be determined by the regression module 112.

At block 206, a regression analysis is performed between physical parameter ratios of known crude oils and corresponding composite compatibility measures to determine coefficients of regression for developing the compatibility model. The composite compatibility measure corresponds to the compatibility parameter K that is to be predicted based on the physical parameter ratios. For example, the regression analysis may be done by the regression module 112.

At block 208, a correlation model and criteria for predicting crude oil blend compatibility is generated based on the regression analysis. For example, the correlation model is the compatibility model that is generated as a mathematical function of the physical parameter ratios, such as log(S)/C, V/C, and A/S, which can be used to predict the value of compatibility parameter K for unknown crude oils. The criteria indicate at which value of K would the crude oil or the blend be incompatible. For example, as equation 1 does not include any constant term, when equation 1 is used as the correlation model, the criteria is K<0 is Incompatible crude oil or blend not having significant heavy oil and K>=0 is compatible crude oil or blend having significant heavy oil. In other examples, a number other than zero may be used for the threshold value of K when a constant term is present. For example, the correlation model and criteria may be generated by the regression module 112.

Based on the generated compatibility model, the prediction module 114 may predict the compatibility of unknown crude oil blends. Further, for increasing heavy oil processing, blends of K>=0 are considered for determining an optimized blend by the optimization module 126. This explained with reference to FIG. 2B.

Referring to method 250 illustrated in FIG. 2B, at block 252, physical parameters are received for one or more unknown crude oils. These physical parameters include at least Sulphur, Viscosity, Carbon content, and API gravity. Based on these physical parameters, various physical parameter ratios can be estimated. In one example, at least Log (S)/C, V/C, API/S are estimated. For example, the physical parameters may be received by the receiving module 110 and the physical parameter ratios may be determined by the prediction module 114. In one example, in case of a blend, the prediction module 114 may first determine the physical parameters for the blend based on the physical parameters for the individual unknown crude oils using mathematical models known in the art, and may then determine the physical parameter ratios for the blend.

At block 254, the physical parameters or physical parameter ratios are used in the correlation model to determine the value of the compatibility parameter K for the unknown crude oil or the blend. For example, the prediction module 114 may use the values of the determined physical parameter ratios in the compatibility model represented by equation 1 to determine the value of the compatibility parameter K for the unknown crude oil or the blend.

Further, at block 256, the blend composition is optimized based on the multi-objective technique as discussed above, which places constraints on values of K, S, V, Pour Point (P), and Vacuum residue Yields (Y). For example, the blend optimization is done by the optimization module 126. By optimizing the values for S, V, P, and Y in addition to keeping K>=0, the optimization module 126 can provide an optimized blend for increasing heavy oil processing in refineries without affecting refinery operations.

The present subject matter will now be illustrated with working examples, which are intended to illustrate the working of disclosure and not intended to be taken restrictively to imply any limitations on the scope of the present disclosure.

EXAMPLES: EXPERIMENTS, RESULTS, AND DISCUSSION

The following discussion is directed to various examples of the present subject matter. Although certain methods and compositions have been described herein as examples, the scope of coverage of this patent is not limited thereto. On the contrary, the present subject matter covers all methods and compositions fairly falling within the scope of the claims either literally or under the doctrine of equivalents.

Example 1: Crude Oil Characterization for Generating Compatibility Model

Crude oil samples were sourced internationally from various part of the world and these samples were received directly from crude oil suppliers/traders and in-house refinery samples. In accordance with the present subject matter, crude oils and blends were characterized for API gravity (ASTM D4052), Sulphur (ASTM D2622, D4294, D5453), Kinematic Viscosity (ASTM D445), Micro Carbon Residue (ASTM D4530), Conradson Carbon Residue Carbon Residue (ASTM D189), Ramsbottom Carbon Residue (ASTM D524), Pour Point (ASTM D97, D5853, D5950), Saturate content, Aromatic content, Resin content and Asphaltene content (IP143) and True Boiling Point (TBP) and PotStill distillation (ASTM D2892 and D5236). Fifty crude oils were characterized and considered for model development. Some of the properties are reported in Table 1 below.

TABLE 1

Characterization data of neat crude oils

| Crude Oils | Origins | A — | S wt % | V cSt @ 40° C. | P ° C. | C wt % | ASPH wt % | Y wt % |
|---|---|---|---|---|---|---|---|---|
| Crude1 | Russia | 31.4 | 1.4 | 10.8 | −21 | 3.88 | 0.74 | 20.48 |
| Crude2 | Nigeria | 35.9 | 0.12 | 3.27 | 13 | 1.05 | 0 | 5.44 |
| Crude3 | UK | 40.3 | 0.26 | 3.25 | −18 | 1.7 | 0.12 | 10.7 |
| Crude4 | Congo | 41.06 | 0.04 | 2.55 | −15 | 0.81 | 0.1 | 13.63 |
| Crude5 | Qatar | 30.2 | 2.15 | 9.1 | −15 | 4.58 | 1.24 | 18.4 |
| Crude6 | Saudi | 24.2 | 3.98 | 32.51 | −34 | 9.5 | 5.09 | 34.29 |
| Crude7 | Angola | 38.7 | 0.19 | 3.64 | −4 | 1.63 | 0.21 | 11.17 |
| Crude8 | Sabah | 36.32 | 0.07 | 2.75 | 11 | 0.13 | 0.03 | 3.27 |
| Crude9 | India | 29.9 | 0.09 | 66 | 40 | 5 | 0.14 | 35 |
| Crude10 | Saudi | 30.41 | 2.48 | 10.41 | −54 | 6.08 | 2.43 | 23.5 |
| Crude11 | Sabah | 38.41 | 0.05 | 2.48 | 18 | 0.01 | 0.06 | 1.96 |
| Crude12 | Qatar | 30.2 | 2.15 | 9.1 | −15 | 4.58 | 1.24 | 18.4 |
| Crude13 | Kuwait | 30.4 | 2.74 | 9.44 | −58 | 6.47 | 2.83 | 24.23 |
| Crude14 | Saudi | 32.03 | 2.23 | 6.85 | −34 | 4.81 | 1.93 | 19.47 |
| Crude15 | Qatar | 23.93 | 3.35 | 29.57 | −9 | 9.58 | 7.1 | 31.88 |
| Crude16 | Yemen | 43.34 | 0.17 | 1.55 | −39 | 0.96 | 0.16 | 6.64 |
| Crude17 | Thailand | 36.2 | 0.06 | 24.91 | 41 | 1.94 | 0.29 | 11.49 |
| Crude18 | Thailand | 41.64 | 0.05 | 3.57 | 21 | 1.17 | 0.35 | 9.3 |
| Crude19 | Saudi | 32.03 | 2.23 | 6.85 | −34 | 4.81 | 1.93 | 19.47 |
| Crude20 | Iran | 30.8 | 1.53 | 9.45 | −21 | 5.57 | 3.57 | 23.23 |
| Crude21 | Cabinda | 30.2 | 0.39 | 10.43 | −17 | 5.26 | 1.8 | 21.04 |
| Crude22 | Azerbaijan | 35.5 | 0.14 | 5.98 | −15 | 1.39 | 0.04 | 12.88 |
| Crude23 | Nigeria | 47.2 | 0.04 | 1.46 | 7 | 0.62 | 0.09 | 1.93 |
| Crude24 | Libya | 36.72 | 0.37 | 4.72 | 3 | 2.82 | 0.17 | 14.87 |
| Crude25 | Saudi | 33.2 | 1.94 | 7.67 | −40 | 4.49 | 1.6 | 17.01 |
| Crude26 | Cabinda | 32.58 | 0.39 | 8.5 | 10 | 3.65 | 0.26 | 20.35 |
| Crude27 | Libya | 36.5 | 0.14 | 9.46 | 27 | 4.53 | 0.21 | 21.34 |
| Crude28 | Abu Dhabi | 39.3 | 0.76 | 3.16 | −7 | 1.76 | 0.29 | 9.61 |
| Crude29 | Qatar | 28.7 | 2.25 | 11.28 | −29 | 5.02 | 0.71 | 20.04 |
| Crude30 | Nigeria | 40.09 | 0.09 | 2.1 | 2 | 0.71 | 0.02 | 2.74 |
| Crude31 | Nigeria | 24.06 | 0.18 | 15.38 | −45 | 2.49 | 0.12 | 11.43 |
| Crude32 | India | 39.2 | 0.14 | 2.4 | 7 | 0.96 | 0.1 | 6.19 |
| Crude33 | India | 27.4 | 0.3 | 6.54 | 2 | 2.52 | 1.13 | 15.44 |
| Crude34 | Saudi | 27.8 | 2.83 | 16.51 | −56 | 7.93 | 4.02 | 29.75 |
| Crude35 | Abu Dhabi | 39.3 | 0.76 | 3.16 | −7 | 1.76 | 0.29 | 9.61 |
| Crude36 | Saudi | 38.09 | 1.22 | 3.2 | −15 | 2.48 | 0.49 | 12.4 |
| Crude37 | Abu Dhabi | 39.21 | 1.32 | 2.87 | −25 | 1.87 | 0.14 | 9.4 |
| Crude38 | Nigeria | 33.09 | 0.18 | 4.53 | −23 | 1.56 | 0.05 | 7.31 |
| Crude39 | Australia | 22.03 | 0.11 | 18.43 | −43 | 0.7 | 0.02 | 5.66 |
| Crude40 | Nigeria | 30.6 | 0.23 | 5.17 | −39 | 1.13 | 0.01 | 6.41 |
| Crude41 | Libya | 40.43 | 0.2 | 3.4 | −1 | 2.12 | 0.61 | 11.04 |
| Crude42 | Iraq | 34.2 | 2.01 | 5.83 | −15 | 3.92 | 0.29 | 18.56 |
| Crude43 | Yemen | 31.8 | 0.59 | 7.88 | −25 | 3.84 | 1.65 | 16.2 |
| Crude44 | Kazakhstan | 41.4 | 0.08 | 3.78 | 13 | 1.83 | 0.23 | 11.6 |
| Crude45 | Brunei | 38.06 | 0.07 | 2.06 | 4 | 0.42 | 0.07 | 2.25 |
| Crude46 | Dubai | 31.99 | 1.86 | 6.05 | −32 | 4.71 | 2.37 | 17.26 |
| Crude47 | Brazil | 19.5 | 0.62 | 129.1 | −29 | 6.89 | 2.25 | 32.45 |
| Crude48 | Sabah | 30.22 | 0.09 | 3.51 | 8 | 0.52 | 0.1 | 2.63 |
| Crude49 | Australia | 47.74 | 0.04 | 1.42 | −12 | 0.36 | 0.03 | 3.09 |
| Crude50 | Sudan | 28.4 | 0.09 | 153.36 | 42 | 6.49 | 0.11 | 41.48 |

In table 1, A = API, S = Sulphur, V = Kinematic Viscosity, P = Pour Point, C = MCCR, ASPH = Asphaltene, Y = VR Yield

Example 2: Crude Oil Compatibility Tests Known in the Art Used for Composite Compatibility Measure Determination Different tests such as colloidal instability index (CII), colloidal stability index (CSI), Stability index (SI), Stankiewicz plot (SP), qualitative-quantitative analysis (QQA), stability cross plot (SCP), spot test, Heithaus parameter, and oil compatibility model (OCM) were carried out for the fifty different crude oils samples. A composite result from multiple of these test results was used for development of the prediction model as per the present subject matter. A brief description of tests used to determine the compatibility of crude oils and their blends are presented below as example 2.1 to 2.9.

Example 2.1: Colloidal Instability Index (CII)

Petroleum oil systems are considered as colloidal solution wherein SARA fractions are important parameters to indicate the status of solution. CII is a function of SARA fraction. It is mathematically expressed as the sum of asphaltene and saturates (flocculants) divided by the sum of aromatics and resins (peptizers) as reported in Eq. (2). Flocculants cause asphaltene destabilization whereas peptizers do stabilize asphaltene fraction. CII is able to predict asphaltene stability as known in the art.

$$CII = \frac{(\text{Asphaltene in wt \%}) + (\text{Saturates in wt \%})}{(\text{Aromatics in wt \%}) + (\text{Resins in wt \%})} \quad \text{Eq (2)}$$

Higher the CII value indicates high saturates or asphaltene and less resins and aromatics and this results in high instability of crude oils. Therefore, the lower the value of CII, higher is the asphaltene stability in crude oils. If CII value is greater than 0.9, asphaltene fraction tends to be unstable within the crude oil. When CII value is less than 0.7, asphaltene is stable and when CII value is in between 0.7-0.9, asphaltene stability is uncertain and is called metastable, as is known in the art.

Example 2.2: Colloidal Stability Index (CSI)

The nature of Asphaltene is a very important parameter for stability of crude oils as highly polar asphaltenes are unstable SARA analysis and polarity of components have been taken into account as shown in Eq. (3) as is known:

$$CSI = \frac{(\varepsilon^{asph})(\text{Asphaltene in wt \%}) + (\varepsilon^{sat})(\text{Saturates in wt \%})}{(\varepsilon^{arom})(\text{Aromatics in wt \%}) + (\varepsilon^{res})(\text{Resins in wt \%})} \quad (3)$$

Here, dielectric constant values (E) for SARA analysis are the following:
For unstable crude oils, $\varepsilon^{asph}$18.4 and $\varepsilon^{res}$=3.8;
For stable crude oils, $\varepsilon^{asph}$=5.5 and $\varepsilon^{res}$=4.7;
For all crude oils, $\varepsilon^{sat}$=1.921 and $\varepsilon^{arom}$=2.379
Further, the stability is estimated as follows:
If CSI>0.95, the crude oil will be unstable, then asphaltene precipitates.
If CSI<0.95, the crude oil will be stable, then asphaltene precipitation is unlikely.

Example 2.3: Stability Index (SI)

SI is expressed as Asphaltene/resins ratio which is useful to quantify the stability of crude oils. It is reported that if Asphaltene/resins ratio is lower than 0.35, then the crude oil will be stable.

Example 2.4: Stankiewics Plot (SP)

In this method, Saturates/Aromatics ratios are plotted against Asphaltene/Resin ratios to observe the tendency of asphaltene precipitation. Regions for stable and unstable are demarked in different zone to find out the status of the sample.

Example 2.5: Sepúlveda Stability Criterion (QQA: Qualitative-Quantitative Analysis)

Sepúlveda stability criteria based on qualitative-quantitative analysis uses different combination of ratios from SARA fractionation: Resin/Asphaltene, Saturates/Asphaltene, Aromatics/Asphaltene, Aromatics/(Saturates/Asphaltene), (Resin/Asphaltene)/(Saturates/Aromatics), and (Saturates/Aromatics)/Asphaltene. Each combination is divided into three zones with a specific value for Resin/Asphaltene. The highest values for crude oils in each combination will be taken into account for next calculations. There were different zones have been created for Stable, Metastable, and Unstable region. As per the Sepúlveda stability criteria, Resin/Asphaltene values for certain crude oil samples are as follows: a) for Stable zone, R/A≥7.2, b) for Metastable zone R/A≥3.2-7.2, and c) for Unstable zone R/A≤3.2. Further, the detailed QQA plots and different criteria for stability as known in the art are shown in table 2 for reference.

TABLE 2

QQA criteria for stability

| Parameters | Stable | Metastable | Unstable |
|---|---|---|---|
| Resin/Asphaltene | >18 | 90-18 | <90 |
| Saturates/Asphaltene | >450 | 225-450 | <225 |
| Aromatics/Asphalteene | >30 | 25-30 | <15 |
| Ssturates/(Aromatics.Asphaltenes) | >120 | 60-120 | <60 |
| (Resin/Asphaltene)/(Saturates/Aromatics) | >0.95 | 0.45-0.95 | <0.45 |
| Aromatics/(Saturates/Asphaltene) | <0.055 | 0.05-0.11 | >0.11 |

Example 2.6: Sepúlveda Stability Criterion (SCP: Stability Cross Plot)

Sepúlveda stability criterion based on Stability Cross Plot uses a number of plots based on SARA fractionation and QQA method to determine the limits between stable and unstable regions. Based on this, following charting is considered to predict the stability as given below
(i) SCP1: [Aromatics/Asphaltene] vs. [(Resin/Asphaltene)/(Saturates/Aromatics)]
(ii) SCP2: [Resin/Asphaltene] vs. [(Resin/Asphaltene)/(Saturates/Aromatics)]
(iii) SCP3: [Resin/Asphaltene] vs. [Saturates/Aromatics]
(iv) SCP4: [Aromatics/(Saturates/Asphaltene)] vs. [(Resin/Asphaltene)/(Saturates/Aromatics)]
Combination of the above criteria will decide the asphaltene stability in crude oils.

Example 2.7: Spot Test

This test is based on visual decision and easy to figure out incompatibility of crude oils and blends. As per ASTM D4740, one drop of the sample is placed on a filter paper Then the filter paper is kept in oven for drying for one hour at 100° C. After that observe the spot is required to be classified according to the following types mentioned in table 3 below.

TABLE 3

Spot test characteristics

| Categories | Spot characteristics |
| --- | --- |
| 1 | Homogeneous spot without inner ring |
| 2 | Faint or poorly defined inner ring |
| 3 | Well-defined thin inner ring, only slightly darker than the background |
| 4 | Well-defined inner ring, thicker than the ring in reference spot No. 3 and somewhat darker than the background |
| 5 | Very dark solid or nearly solid area in the center. Central area is darker than the background |

According to this method, if a spot is classified into category 3 or higher categories, then the crude oil will be incompatible.

Figure 3:
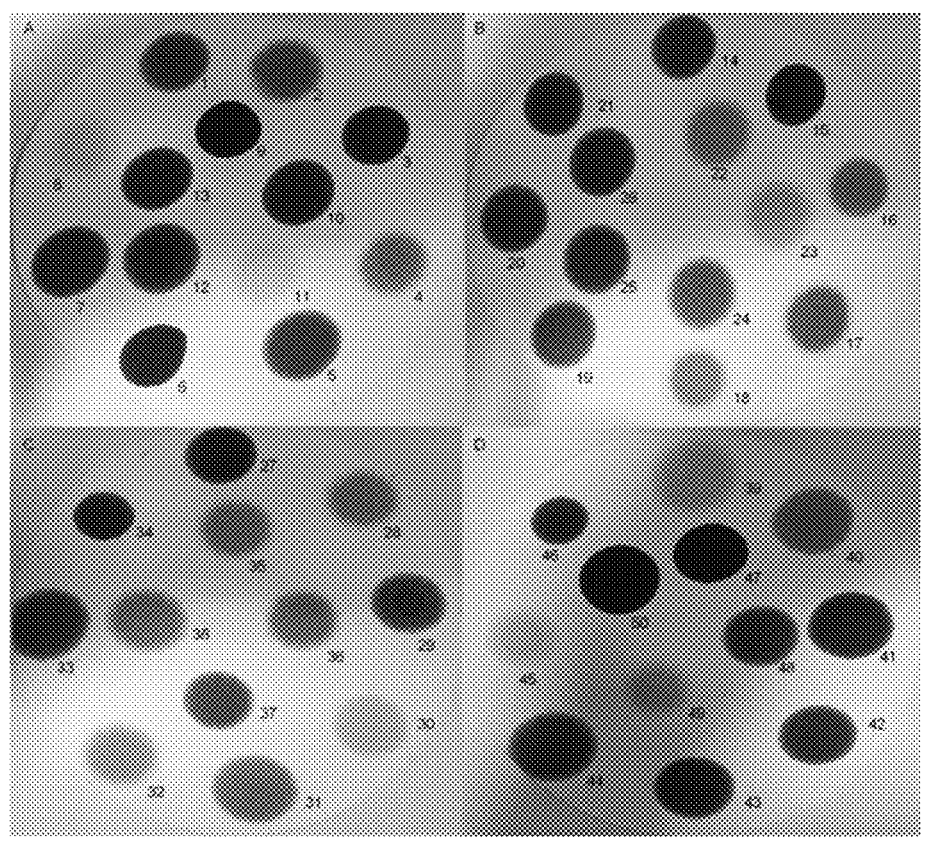
FIG. 3 illustrates Spot tests of 50 crude oils (conducted in four sets: A, B, C, D), in accordance with an example implementation of the present subject matter.

Using this method, spot tests of fifty crude oils were carried out and are depicted in FIG. 3. The tests were done in four groups represented as A, B, C, D since all fifty could not be carried out together. The light crude oil and heavy crude oil can be easily differentiated based on intensity of shades. The dark black color is representing heavy crude oil and light shade corresponds to light crude oil. Similarly, the asphaltene flocculation, precipitation and its compatibility/incompatibility can also be identified based on shades of spot.

Example 2.8: Heithaus Parameter (Parameter P)

In this method, a solution of oil in an aromatic solvent (toluene) is titrated with paraffinic solvent (n-heptane) until asphaltene precipitation occurs' A flocculation ratio (FR) is estimated at this point taking into account the volumetric fraction of the toluene in relation to the total volume of solvent ($V_S$) and the titrant volume ($V_T$) as reported in Eq. (4). This method was developed by Heithaus to predict the stability of heavy oils.

$$FR = \frac{V_s}{V_s + V_T} \qquad \text{Eq. (4)}$$

Concentration of petroleum or bitumen in an aromatic solvent (C) is given by the mass of crude oil divided by the total volume of aromatic solvent and titrant as follows in Eq. (5):

$$C = \frac{W_A}{V_s + V_T} \qquad \text{Eq. (5)}$$

where $V_S$ is the volume of the solvent,
$V_T$ is the volume of the titrant, and
$W_A$ is the mass of oil in the sample.

The titration is repeated at least four times with different concentration of oil. Values for FR and C at each concentration are plotted and a linear regression is done through the four points to give the intersection with FR and C axes. The intersection with FR axis is denoted as $FR_{max}$ whereas the intersection with the C axis is $C_{min}$. $FR_{max}$ is the ratio of sol-vent to titrant at which oil is soluble in all concentrations, and $C_{min}$ is the minimum amount of oil added to the titrant to remain fully soluble. $C_{min}$ could be considered as the onset of asphaltene precipitation (OAP) because it is the minimum volume of n-heptane per oil mass (mL/g) to cause precipitation with no presence of toluene In the onset of asphaltene precipitation, $V_S$ is zero and the sample is only conformed by bitumen and titrant. Afterwards, $P_a$, $P_0$, and P are calculated, where $P_a$ is the solubility of asphaltenes in bitumen and is expressed as follows as shown in Eq. (6):

$$P_a = 1 - FR_{max} \qquad \text{Eq (6)}$$

More insoluble molecules are present in oil with low values of Pa. $P_0$ is the solubility power of maltenes in oil. The higher the $P_0$ value, the higher the solubility power. $P_0$ is calculated by Eq. (7):

$$P_0 = FR_{max}\left[\left(\frac{1}{C_{min}}\right) + 1\right] \qquad \text{Eq (7)}$$

Finally, Heithaus parameter P is calculated with Eq. (8) and represents the stability of oil:

$$P = \frac{P_0}{(1 - P_a)} \qquad \text{Eq (8)}$$

When P<1, crude oil is unstable (low colloidal stability) and the sample is prone to asphaltene precipitation. On the contrary, for higher values of P, oil will be more stable with high asphaltene peptization.

Example 2.9: Oil Compatibility Model (OCM)

The OCM is based on estimation of two parameters as (i) insolubility number ($I_N$), and (ii) solubility blend number ($S_{BN}$). $I_N$ represents the extent of asphaltenes insolubility, and $S_{BN}$ is related to the crude oil capacity for solubilizing asphaltenes in solutions of crude oil and n-heptane with toluene In this method, solutions containing n-heptane and toluene in different ratios are added to the crude oil in order to determine the onset of asphaltene precipitation. Two tests are needed at least: (a) heptane dilution (HD) test, and (b) toluene equivalence (TE) tests for estimation of $S_{BN}$ and $I_N$. When using this test, the mixture of n-heptane/toluene is called "test liquid" and for each volume ratio of oil ($V_{oil}$) to test liquid ($V_{TL}$), the minimum volume of toluene to keep asphaltenes in solution is determined. Based on these experiments, following linear equation is derived, where the linear coefficient represents the $I_N$ as represented in Eq. (9).

$$\frac{100 \ V_T}{V_{TL}} = I_N + \frac{100 \ V_{oil}}{V_{TL}}\left[\frac{(I_N - S_{BN})}{100}\right] \qquad \text{Eq (9)}$$

The minimum percent of toluene in the TL to keep asphaltenes soluble is plotted [$100*(V_T/V_{TL})$] against 100 times the volume ratio of oil to test liquid [$100*(V_{oil}/V_{TL})$], the data will follow on a line and the y-axis intercept is equal to the $I_N$, a line and the y-axis intercept is equal to the $I_N$, while the x-axis intercept is HD. This term is used to estimate the $S_{BN}$ as represented in Eq. (10).

$$S_{BN} = I_N + \left[1 + \frac{100}{H_D}\right] = I_N\left[1 + \frac{V_H}{V_{oil}}\right]V_{T=0} \qquad \text{Eq (10)}$$

$H_D$ is calculated by x-axis intercept directly by determining the maximum volume of n-heptane that causes asphaltene precipitation. The $S_{BN}/I_N$ ratio is used for predicting the pure oil stability, a higher value will indicate more stable crude oils.

As can be observed, the various tests in the prior art, except the spot test, rely on chemical composition analysis and, in particular, SARA estimation. These tests provide numerical outputs which are then analysed based on different criteria to determine compatibility. Further, the compatibility as determined by the different tests can differ and hence, usually multiple tests are carried out in the prior art and the average result is used to determine compatibility. For example, if as per the result of two tests, a crude oil is found to be incompatible and as per four other tests it is found to be compatible, then the oil is determined to be compatible overall.

In contrast, the present subject matter allows determination of compatibility based on physical parameter ratios, without SARA analysis, based on the compatibility model. To generate the compatibility model, the fifty crude oils mentioned in table 1 were subjected to the nine tests mentioned above in this example. Other than spot test, numerical results were obtained for all tests and based on their respective criteria the compatibility of each oil was determined. Further, a composite compatibility measure was obtained for each oil from the numerical results, which was representative of the average of compatibility determined by the different tests for that oil.

The composite compatibility measure could be the result of any mathematical function of the numerical results as would be understood by a person skilled in the art and is not limited to a particular mathematical function. In the present example, the composite results of primarily numerical based methods along with stability criterions including CSI, SI, SP, QQA, and SCP have been considered for regression. Further, the K model has been tuned by subtracting with constant obtained by regression to fix the compatibility criteria. This composite compatibility measure, corresponding to the compatibility parameter K, was then used for developing the compatibility model. Further, it was surprisingly found that the compatibility parameter K thus determined was also positively correlated to and could predict the intensity of the spot obtained in the spot test. To develop the compatibility model, the impact of different physical parameters on the composite compatibility measure was determined as explained in the next example.

Example 3: Impact of Physical Parameter Ratios on Compatibility (Stability)

Every crude oil variety differs from the other in terms of composition and properties. The quality of crude oils varies considerably and depends upon the oil source and its characteristics. The physical parameters included in the study are mainly, API gravity (API or A), Sulphur (S), Viscosity (V) and Carbon Residue (C) Depending upon nature and quality of crude oils, compatibility of crude oil and blends gets affected.

It is known that the parameters individually can impact compatibility and stability of crude oil blends. For example, API gravity has a high impact on deciding whether crude is light or heavy, which is thought to have a direct relation with compatibility. Sulphur has a high influence in the middle distillate range and moreover, this also has an impact on behaviour of crude oils. Generally, high sulphur crude oils are high in naphthenic hydrocarbons and low sulphur crude oils are observed to include more of paraffinic or aromatic hydrocarbons It also impacts the amount of asphaltene content in crude oils and their stability. Viscosity is also one of the important parameters for deciding whether a crude oil is light or heavy oil and it has an impact on the stability of crude oils Carbon residue is related to high aromatic content and therefore this can act as solvent to keep asphaltene in the solution and therefore the amount of carbon residue in the oil is an important parameter for stability of oil However, in the art, the effect of ratios of the physical parameters has not been considered. In the present subject matter, it has been surprisingly found that some of the ratios of the physical parameters have a surprising effect on the compatibility/stability of crude oils as will be discussed further.

The fifty oil samples reported in Table 1 above were characterized for physical parameters. These physical parameters were arranged in different ratios, such as API/S, SN, C/API, C/S, 1/C, log (S)/C, V/API, and V/API, to predict crude oil compatibility. Further, different compatibility tests as mentioned in Example 2 were carried out using all these crude oil samples. The composite compatibility measure was used for creating the prediction model. Regression between physical parameter ratios and composite compatibility result was carried out to generate the coefficients.

Figure 4:
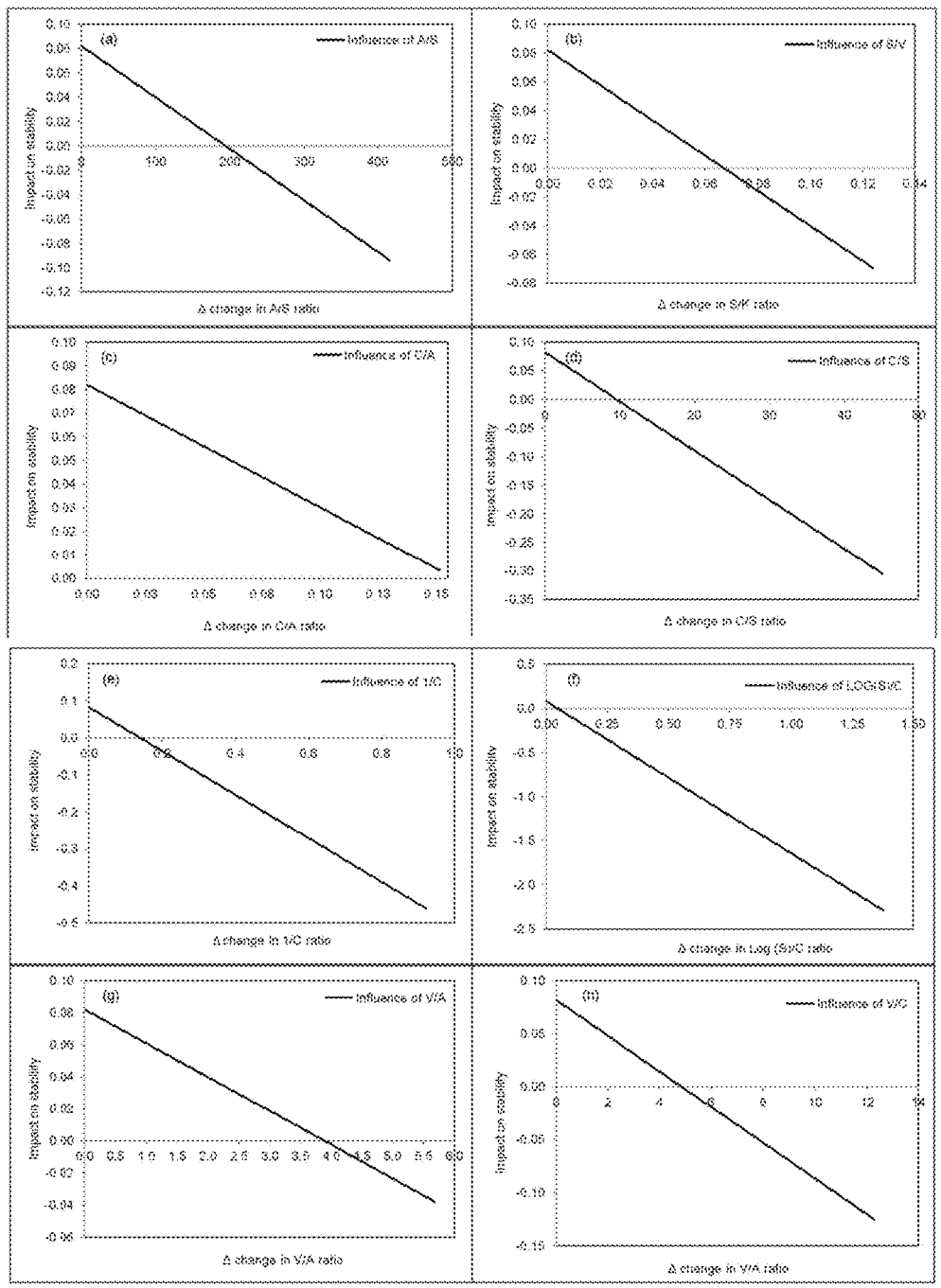
FIG. 4 illustrates impact of various physical parameter ratios on crude oil compatibility with (a) Effect of API/S; (b) Effect of S/V; (c) Effect of C/API; (d) Effect of C/S; (e) Effect of 1/C; (f) Effect of Log (S)/C/; (g): Effect of V/API; (h) Effect of V/C, in accordance with an example implementation of the present subject matter.

The experimental compatibility data considered in the study is based on average results of the eight different test methods (other than spot test) mentioned in Example 2. FIG. 4 plots (a) to (h) illustrate graphs depicting the influence of the physical parameter ratios of crude oils on compatibility/stability of the oil. This study helped to develop an understanding about the impact of physical parameter ratios on compatibility and selection of most suitable physical parameter ratios for regression with the composite compatibility measure for determining the crude oil compatibility parameter (K). The prediction model thus developed to predict K based on the physical parameter ratios is also referred to as compatibility model.

The graphs shown in FIG. 4 depict the change in composite compatibility measure, which is the K value, due to a change in physical parameter ratios of the crude oil. The independent variables in the graphs represent the change in physical parameter ratios of the crude oil and the dependent variable represents the change in K value of the crude oil. Further, the graphs are derived purely for studying the impact caused on K value due to physical parameter ratios in terms of magnitude. Therefore, the dependent and independent variables represent the deviation in the values. In other words, the dependent variable Y equals $\Delta y$, where y is the K value being studied and the independent variable X equals $\Delta x$, where x is the physical parameter ratio. The plots of FIG. 4 are now discussed in detail.

FIG. 4(a) illustrates the impact of change in A/S of crude oil on the K value. A change in the value of A/S yields a change in the K value, as shown in the figure. For a given crude oil, the change in A/S may be varied up to 400 units.

However, individually, the change in API gravity of a typical crude oil can be varied from 10-60 units and the change in sulphur value of a typical crude oil can be varied from 0.001-5.0 units. The relationship between the change in A/S and change in K value is found to be linear. For a given crude oil, there is a change of 0.08 units of K value noted due to a change in 200 units of A/S. However, on the negative scale, K changes up to −0.10 units.

FIG. 4(b) and FIG. 4(c), illustrate the impact on K value of the crude oil due to change in S/V and C/A of crude oil respectively. There is a low impact observed for these parameter ratios. In this case, there is a maximum of −0.1 to 0.08 units of change in K value observed due to a change in these physical parameter ratios of crude oil.

Further, on studying the influence of the various physical parameter ratios of crude oil on K value, it is observed that each parameter influences the K value on a different scale. For example, FIG. 4(d), FIG. 4(e) and FIG. 4(f) illustrates the impact of change in C/S, 1/C and Log (S)/C in crude oil on the K value. For a given crude oil, a change of 0.3 units of C/S influences the K value. It is noted that a change in −0.30 to 0.08 units of K value can be got due to change in C/S. Similarly, a −0.5 to 0.08 units of change in the K value can be got due to change in 1/C. When Log (S)/C ratio is changed in a crude oil, a very high influence in the K value of crude oil observed. A change of 0 to −2.5 units in K value, which denotes a very high influence in comparison with other parameter ratios and therefore this parameter ratio has highest impact on compatibility.

FIG. 4(g) and FIG. 4(h), illustrate the impact on K value of crude oil due to change in V/API, and V/C of crude oil. There is a small impact observed with change in V/API. In this case, there is a maximum of −0.040 to 0.08 units of change in K value due to change in V/API ratio of crude oil. However, there is change of −0.12 to 0.08 units change in K value observed with change in V/C ratio of crude oil.

Thus, it can be inferred that the K value of crude oil and blends is more sensitive to a change in the A/S, C/S, log (S)/C, 1/C and V/C physical parameter ratios. For a given crude oil, typically the API, Sulphur content, CCR content and Viscosity may be changed up to 30 units, 5 units, 10 units and 200 units, respectively. This may be attributed to the fact that the different components vary within different ranges across compositions of crude oils and further, the different physical parameters are affected to different extents by changes in compositions of the crude oils.

Based on the relationship between physical parameter ratios of crude oil and composite compatibility measure, K value, of crude oil as illustrated in FIG. 4(a)-FIG. 4(h), appropriate physical parameters have been chosen for developing the correlation model for prediction of compatibility, also referred to as compatibility model. The physical parameter ratios selected for the prediction of compatibility together include the parameters A, S, V, and C. For example, physical parameter ratios chosen for developing correlation model includes at least A/S, log (S)/C, and V/C. In one example, additional physical parameter ratios along with any of other parameters such as pour point may also be used. The physical parameter ratios of crude oils in appropriate combinations are used for developing the correlation model. The correlation model parameter K has no dimension and it only takes numerical values of physical parameter ratios to predict K value. The correlation model is then used for predicting crude oil compatibility of unknown crude oils or blends.

Example 4: Modeling for Prediction of Crude Oil Blend Compatibility

The physical parameter ratios of known crude oils were experimentally measured as reported in table 1. Further, the values of physical parameter ratios were determined. The physical parameter ratios include A/S, log (S)/C, and V/C. Data for other parameters including Saturate content, Aromatic Content, Resin Content, Asphaltene Content, Pour Point, and Vacuum Residue yield, etc. of the known crude oils was also determined. Different compatibility test data viz. CII, CSI, SP, QQS, SCP, Heithaus parameter (or parameter P), and oil compatibility model (OCM) as discussed in Example 2 were used to obtain the composite compatibility measure. Regression analysis was performed between the measured physical parameter ratios of crude oils and composite compatibility of the crude oils. The coefficients of regression were calculated to obtain the model. The model development approach is depicted in method described above with reference to FIG. 2A.

Theoretically, the correlation model is written as, K=f (at least A/S, log (S)/C, and V/C), where, K denotes compatibility of crude oil. In one example, the correlation model may be written as $$K = f(\log(S)/C, A/S, \text{ and } V/C).$$

In another example, other combinations of physical parameters may be used.

The correlation model can be then used in the method for predicting compatibility of crude oil as illustrated and described above with reference to FIG. 2B.

Example 5: Model Validation

The model developed as discussed above was used to predict the compatibility of a second set of crude oils and blends and the result was validated against the composite results of the second set of crude oils and blends based on the prior art tests discussed in Example 2 above. Validation was done using unknown test samples and was found to be valid for 97% of the test samples.

Example 5.1. Crude Oil Characterization

Sixteen crude oils were used for validation. The crude oils were characterized to determine their physical parameters as reported in table 4.

TABLE 4

| Characterization of neat crude oils (light and heavy) | | | | | | | | | | | |
|---|---|---|---|---|---|---|---|---|---|---|---|
| | Crude | | A | S | V | P | C | Y | Hydrocarbon Analysis (wt %) | | |
| SN | Oils | Origins | — | wt % | cSt | ° C. | wt % | wt % | Sa | Ar | R | As |
| C1 | AH | Saudi Arabia | 27.54 | 2.51 | 17.90 | −45 | 8.46 | 28.26 | 48.09 | 35.28 | 10.76 | 5.88 |

TABLE 4-continued

Characterization of neat crude oils (light and heavy)

| SN | Crude Oils | Origins | A — | S wt % | V cSt | P °C. | C wt % | Y wt % | Hydrocarbon Analysis (wt %) | | | |
|---|---|---|---|---|---|---|---|---|---|---|---|---|
| | | | | | | | | | Sa | Ar | R | As |
| C2 | AEL | Saudi Arabia | 37.29 | 0.97 | 3.61 | −54 | 1.68 | 8.19 | 59.11 | 35.56 | 4.86 | 0.48 |
| C3 | AL | Saudi Arabia | 32.93 | 1.75 | 5.98 | −55 | 4.48 | 18.09 | 41.74 | 42.82 | 12.97 | 2.48 |
| C4 | Ratawi | Saudi-Kuwait Neutral Zone | 23.94 | 3.88 | 32.39 | −15 | 10.07 | 33.82 | 35.62 | 42.05 | 14.47 | 7.87 |
| C5 | SB | Algeria | 42.35 | 0.16 | 2.18 | −39 | 1.08 | 7.33 | 62.97 | 25.81 | 11.04 | 0.18 |
| C6 | RG | Egypt | 21.44 | 3.49 | 83.70 | 6 | 10.60 | 34.25 | 23.78 | 40.29 | 27.35 | 8.58 |
| C7 | Murban | Abu Dhabi | 37.86 | 0.89 | 3.68 | −37 | 1.85 | 9.01 | 43.89 | 36.97 | 18.60 | 0.54 |
| C8 | RJ | India | 29.90 | 0.09 | 66 | 40 | 5.00 | 35.00 | 79.12 | 7.52 | 12.03 | 1.34 |
| C9 | ML | Yemen | 42.60 | 0.12 | 2.50 | −35 | 1.05 | 7.32 | 43.89 | 32.69 | 23.19 | 0.23 |
| C10 | Erha | Nigeria | 31.62 | 0.24 | 5.37 | −33 | 1.16 | 8.81 | 54.37 | 24.13 | 21.33 | 0.17 |
| C11 | MH | India | 39.85 | 0.13 | 2.54 | 12 | 1.11 | 8.00 | 45.37 | 34.48 | 20.01 | 0.15 |
| C12 | Antan | Nigeria | 28.15 | 0.32 | 8.68 | −12 | 3.05 | 17.46 | 43.61 | 37.16 | 18.72 | 0.51 |
| C13 | Mascila | Yemen | 31.74 | 0.69 | 8.20 | −3 | 3.91 | 18.68 | 45.31 | 38.10 | 15.18 | 1.41 |
| C14 | Kuwait | Kuwait | 31.05 | 2.26 | 7.45 | −27 | 6.47 | 23.54 | 38.63 | 46.44 | 11.04 | 3.89 |
| C15 | AM | Saudi Arabia | 30.49 | 2.78 | 8.75 | −50 | 5.07 | 20.57 | 41.63 | 44.15 | 11.66 | 2.56 |
| C16 | NB | Sudan | 31.50 | 0.08 | 79.60 | 28 | 4.86 | 33.96 | 45.56 | 33.49 | 19.66 | 1.29 |

Crude Oils:
AH = Arab Heavy, AEK = Arab Extra Light, AL = Arab Light, SB = Saharan Blend, RG = Ras Gharib, RJ = Rajasthan, ML = Marib Light, MH = Mumbai High, AM = Arab Mix, NB = Nile Blend, Parameters: A = API, S = Sulphur, V = Kinematic Viscosity, P = Pour Point, C = MCCR, Y = VR Yield, Sa = Saturates, Ar = Aromatics, R = Resins, As = Asphaltene It has been observed that API is not the only indication in crude oils of whether they are heavy or light oils. The vacuum residue yields, pour point, viscosity of the crude oils are also an indication of type of oils. For example, high vacuum residue yields indicate heavy crude oils and low vacuum residue yield indicates light crude oils. Similarly, high viscosity and high pour point indicates heavy crude oils. From Table 4, five crude oils (AH, Ratawi, RG, RJ and NB) have been identified as heavy crude oils. Viscosities of these crude oils are observed to be higher than 10 cSt. With respect to pour point, only RJ and NB are indicated to be heavy oils. It is also known that heavy crude oils have high asphaltene content. Among five heavy crude oils, AH, Ratawi and RG have higher asphaltene content and RJ and NB have lower asphaltene content.

Thus, heavy crude oils can be further classified in two types (i) non-asphaltenic and (ii) asphaltenic heavy crude oils. These two types need to be dealt with using different approaches. Non-asphaltenic heavy crude oils have mainly high viscosity, high pour point, and high vacuum residue yields, which make the crude oils difficult to handle and are normally addressed by blending with suitable light and non-asphaltenic crude oils. High asphaltenic heavy crude oils, however, cause asphaltene precipitation and fouling related problems when they are blended with non-asphaltenic crude oils or light crude oils and are hence generally incompatible with other crudes for blending. However, using the present subject matter, the processing of asphaltenic heavy crude oils can also be increased and they can also be used in optimized blends determined using the techniques disclosed herein.

SARA characterization as known in the art is one of the ways to understand the types of oil and its compatibility as reported in Table 4. It is known that when SARA fraction is in appropriate proportion, crude oil or blends are compatible. Naturally occurring crude oils, even without blending with any other crude oils can also be incompatible called self-incompatible crude oils when their SARA fraction is imbalanced. Heavy oils, which as such may not create problem of asphaltene precipitation problems and might be stable, may still not be suitable for processing due to refinery configuration limitations. Hence, such heavy oils may not be processed as they are not suitable to meet the processing and profitability requirements.

In the present subject matter, the compatibility model based on compatibility parameter K can be used to not only identify the types of crude oils, i.e., whether they are light or heavy, but it also estimates the optimal composition for meeting blend compatibility when two or more than crude oils are blended.

Example 5.2 Estimation of Crude Oil Compatibility Based on Known Techniques

Based on SARA analysis, various compatibility parameters have been calculated to predict the compatibility as reported in table 5. In the present example, six different methods such as (i) CII, (ii) CSI, (iii) SI, (iv) SP, (v) QQA, (vi) SCP, have been used to obtain the composite compatibility measure of the sixteen crude oils characterized in table 4. The results of the compatibility tests are shown in table 5 below. In the table, the numbers are rounded off to first decimal place.

TABLE 5

Estimation of compatibility measures using SARA for sixteen crude oils

| Crude oils | CII | CSI | S/Ar | A/R | R/A | S/A | Ar/A | Ar/(S/A) | (R/A)/(S/Ar) | S/(Ar*A) | S + A | R + Ar |
|---|---|---|---|---|---|---|---|---|---|---|---|---|
| AH | 1.2 | 1.27 | 1.4 | 0.55 | 1.8 | 8.2 | 6.0 | 4.3 | 1.3 | 0.2 | 54.0 | 46.0 |
| AEL | 1.5 | 1.13 | 1.7 | 0.10 | 10.2 | 123.7 | 74.4 | 0.3 | 6.1 | 3.5 | 59.6 | 40.4 |
| AL | 0.8 | 0.70 | 1.0 | 0.19 | 5.2 | 16.8 | 17.3 | 2.5 | 5.4 | 0.4 | 44.2 | 55.8 |
| Ratawi | 0.8 | 1.02 | 0.8 | 0.54 | 1.8 | 4.5 | 5.3 | 9.3 | 2.2 | 0.1 | 43.5 | 56.5 |
| SB | 1.7 | 1.14 | 2.4 | 0.02 | 62.6 | 357.2 | 146.4 | 0.1 | 25.7 | 13.8 | 63.1 | 36.9 |
| RG | 0.5 | 0.72 | 0.6 | 0.31 | 3.2 | 2.8 | 4.7 | 14.5 | 5.4 | 0.1 | 32.4 | 67.6 |
| Murban | 0.8 | 0.55 | 1.2 | 0.03 | 34.5 | 81.5 | 68.6 | 0.5 | 29.1 | 2.2 | 44.4 | 55.6 |
| RJ | 4.1 | 2.46 | 10.5 | 0.11 | 9.0 | 59.2 | 5.6 | 0.1 | 0.9 | 7.9 | 80.5 | 19.5 |
| ML | 0.8 | 0.50 | 1.3 | 0.01 | 99.8 | 188.9 | 140.7 | 0.2 | 74.4 | 5.8 | 44.1 | 55.9 |
| Erha | 1.2 | 0.72 | 2.3 | 0.01 | 127.7 | 325.6 | 144.5 | 0.1 | 56.7 | 13.5 | 54.5 | 45.5 |
| MH | 0.8 | 0.53 | 1.3 | 0.01 | 134.7 | 305.4 | 232.1 | 0.1 | 102.4 | 8.9 | 45.5 | 54.5 |
| Antall | 0.8 | 0.54 | 1.2 | 0.03 | 36.8 | 85.7 | 73.0 | 0.4 | 31.4 | 2.3 | 44.1 | 55.9 |
| Mascila | 0.9 | 0.67 | 1.2 | 0.09 | 10.7 | 32.1 | 27.0 | 1.2 | 9.0 | 0.8 | 46.7 | 53.3 |
| Kuwait | 0.7 | 0.77 | 0.8 | 0.35 | 2.8 | 9.9 | 11.9 | 4.7 | 2.4 | 0.2 | 42.5 | 57.5 |
| AM | 0.8 | 0.72 | 0.9 | 0.22 | 4.6 | 16.2 | 17.2 | 2.7 | 4.3 | 0.4 | 44.2 | 55.8 |
| NB | 0.9 | 0.64 | 1.4 | 0.07 | 15.2 | 35.2 | 25.9 | 1.0 | 20.7 | 1.1 | 46.9 | 53.1 |

Crude Oils:
AH = Arab Heavy, AEK = Arab Extra Light, AL = Arab Light, SB = Saharan Blend, RG = Ras Gharib, RJ = Rajasthan, ML = Marib Light, MH = Mumbai High, AM = Arab Mix, NB = Nile Blend,
Parameters:
S = Saturates, Ar = Aromatics, R = Resins, As = Asphaltene CII of crude oils have been estimated using Eq. (2). CII data for RJ crude oil is observed to be very high (4.1) as compared to other crude oils (approx. 1) and in turn the method suggests that this crude oil is highly unstable and incompatible. However, CII is higher due to higher saturate contents of RJ while the asphaltene content is low as shown in table 4. When crude oils have high saturate content with low asphaltene content, asphaltene precipitation does not take place and crude oils are observed to be stable and form compatible blends. In another case, RG crude oil has low saturate content but is high in asphaltene content. However, CII value is low and this indicates RG crude oil is stable and compatible. In prior art also, it is reported that CII may not be appropriate for determining stability/compatibility when saturates are very high or very low and asphaltenes are very low. In such cases, CII method fails to accurately predict the compatibility of crude oils. CII method may be good for certain range of SARA fraction and this one test is inadequate to make decision about compatibility of crude oils. Hence, along with CII, other test results are considered.

CSI of crude oils have been estimated using Eq. (3). This is an improved method over CII wherein the correlation has been classified for different SARA fractions for accurate prediction of compatibility. According to this method, AH, AEL, Ratawi, SB and RJ crude oil are unstable and others are stable including RG crude oil with asphaltene content.

According to SI method (Asphaltene/Resin ratio) and criteria mentioned in example 2.3, AH and Ratawi crude oils are found unstable, Kuwait is Metastable and other remaining crude oils are stable.

Figure 5:
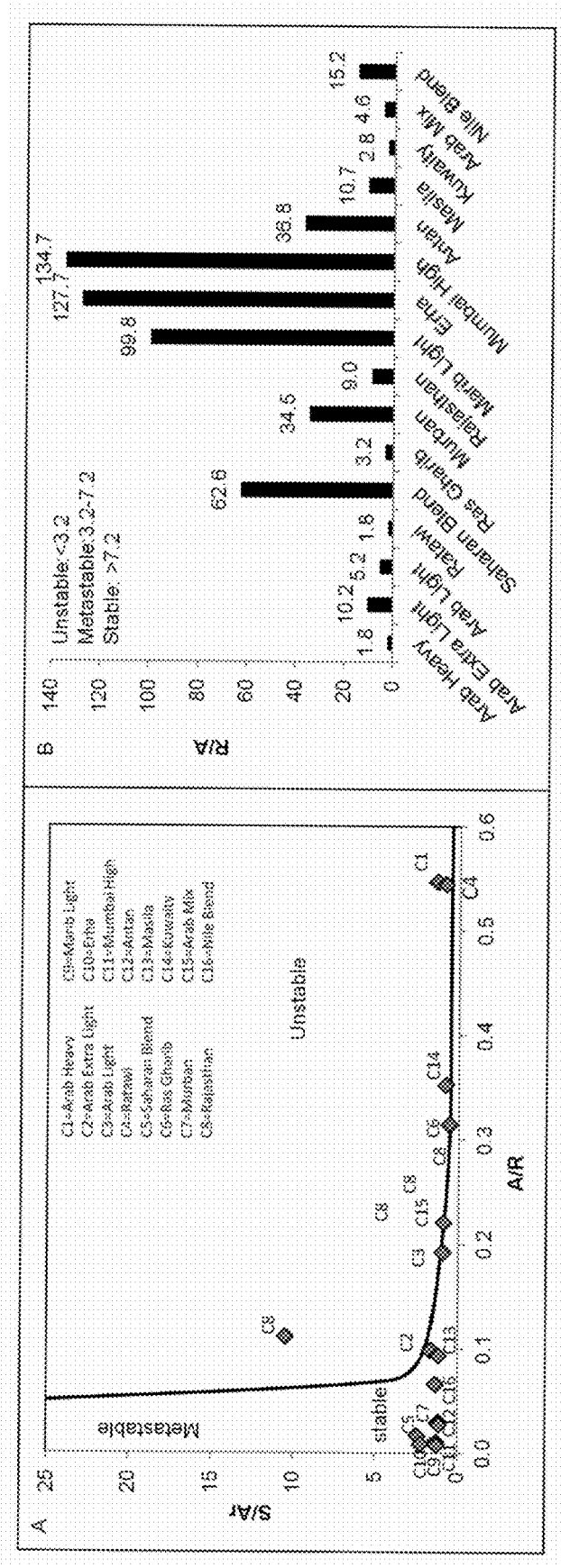
FIG. 5 illustrates plots of Stability criteria: (A) Stankiewicz plot (SP) and (B) Sepulveda chart for sixteen crude oils, in accordance with an implementation of the present subject matter.

Plot of Saturates/Aromatics and Asphaltenes/Resin have been plotted in FIG. 5. According to SP criteria, AH, Ratawi, Ras Gharib, Rajasthan, Kuwait and AM are unstable and other remaining crude oils are stable. In the similar line, according to Sepulveda criteria, AH, Ratawi, Kuwait found to be unstable, AL, Ras Gharib and AM crude oils are Metastable and remaining crude oils are stable.

Figure 6:
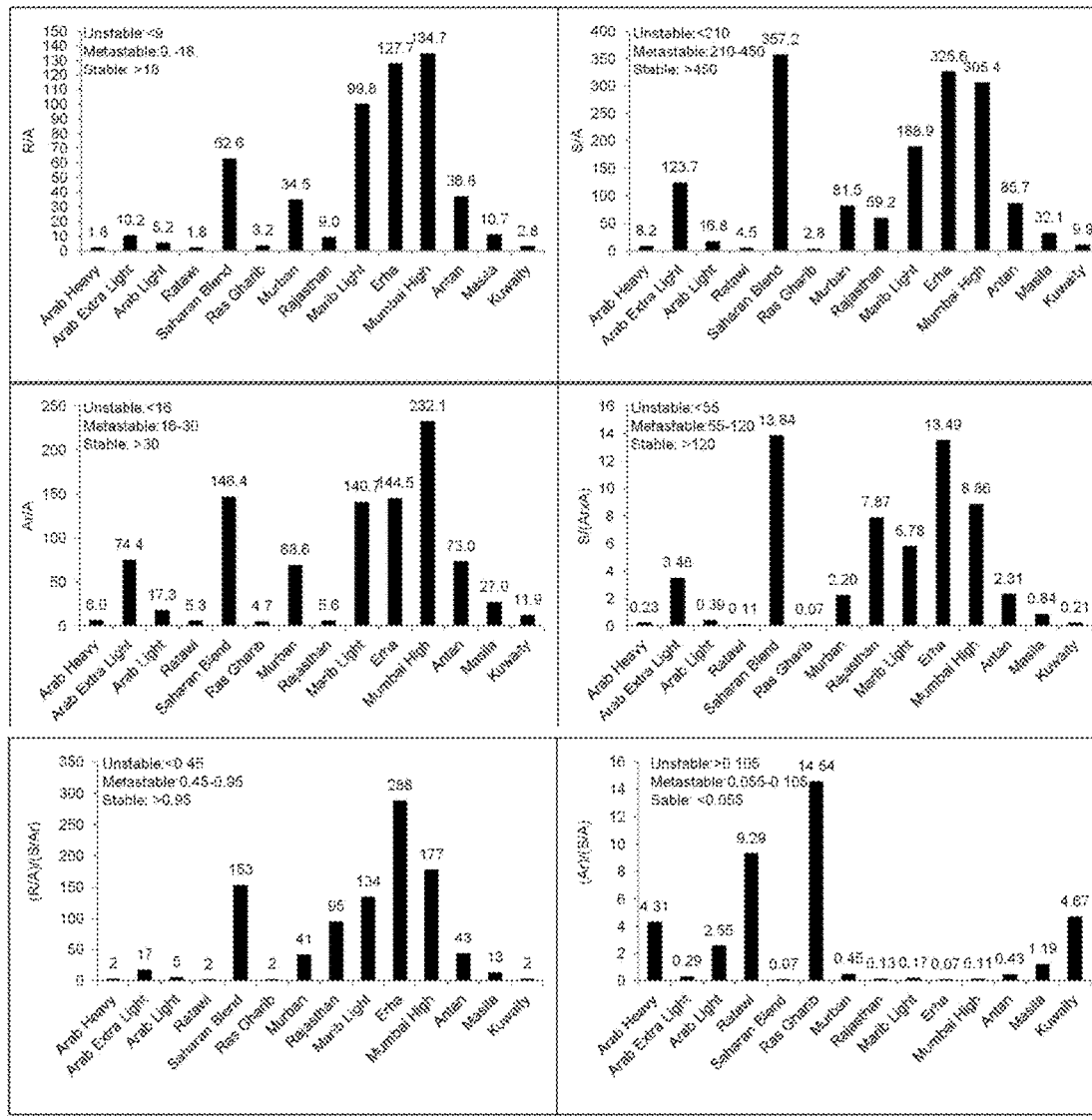
FIG. 6 illustrates Plots of QQA: (i) Resin/Asphaltene; (ii) Saturates/Asphaltene; (iii) Aromatics/Asphaltene; (iv) Saturates/(Aromatics.Asphaltene); (v) (Resin/Asphaltene)/(Saturates/Aromatic s); (vi) (Aromatics)/(Saturates/Asphaltene) for sixteen crude oils, in accordance with an implementation of the present subject matter.

QQA analysis was carried out based on six different relationship of SARA fraction as per method described in example 2.5 and criteria mentioned in table 2. The relationships have been depicted in FIG. 6. According to the overall result of this method, AH, AL, Ratawi, RG, RJ, Mascila, Kuwait and AM are determined to be unstable, AEL, Murban, ML, Antan and NB are determined to be Metastable and remaining are determined to be stable.

Figure 7:
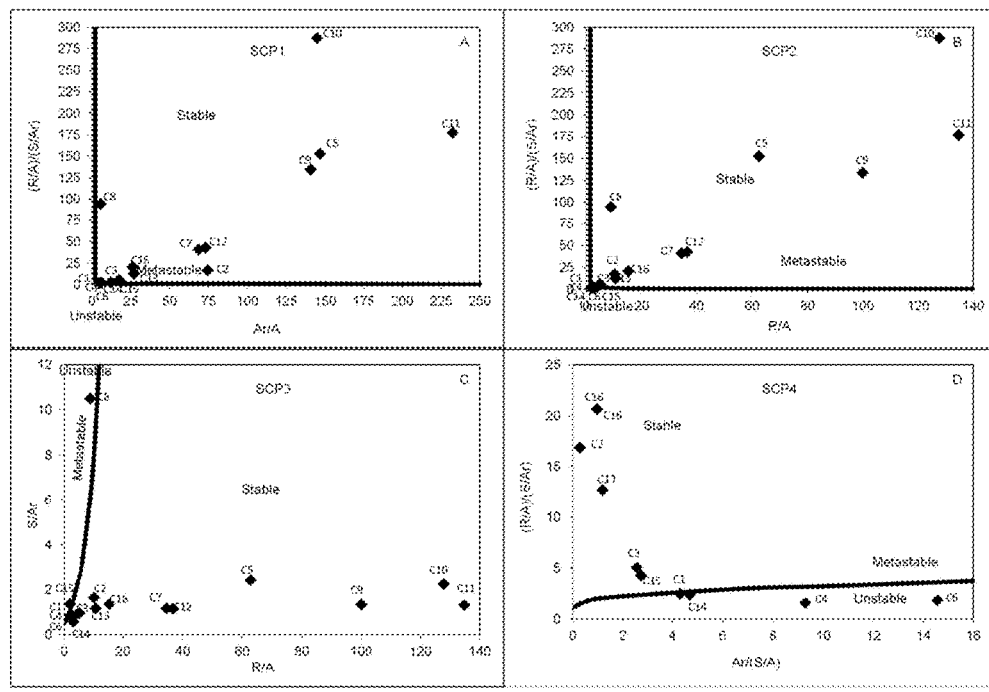
FIG. 7 illustrates Plots of SCP: (i) (Resin/Asphaltene)/(Saturates/Aromatics) vs. Aromatics/Asphaltene; (ii) (Resin/Asphaltene)/(Saturates/Aromatics) vs. Resin/Asphaltene; (iii) Saturates/Aromatics vs. Resin/Asphaltene; (iv) (Resin/Asphaltene)/(Saturates/Aromatics) vs. (Aromatics)/(Saturates/Asphaltene) for sixteen crude oils, in accordance with an implementation of the present subject matter.

Stability Cross Plot (SCP) analysis is carried out based on four different relationships of SARA fraction criteria. According to this method, four different charts SCP1, SCP2, SCP3 and SCP4 indicate different compatibility results as per FIG. 7. The overall results of this method indicate that AH, Ratawi and RG are unstable, and other remaining crude oils are stable.

Example 5.3 Comparison of Results of Known Techniques with Results of K Model

The K value was determined based on compatibility model represented by equation 1 for the sixteen crude oils. The results of compatibility parameter K were compared with the compatibility results based on SARA analysis and spot test. It is known that any one test method is inadequate to make accurate decision for compatibility of crude oil and blends. In this case, individual and composite results of all these prior art tests have been considered for validation of K model. The test results of the sixteen crude oils are reported in table 6. Additionally, some of the sixteen crude oils were also processed in a refinery and the observation of whether it was compatible/stable during processing is also provided in table 6 where applicable.

TABLE 6

Comparison of K model with results obtained from different compatibility tests

| Crudes | CII | CSI | SI | QQA | SP | SCP | Spot Test | Composite Result | K model Results | Refinery Experience |
|---|---|---|---|---|---|---|---|---|---|---|
| AH | U | U | U | U | U | U | U | U | U | U |
| AEL | U | U | S | M | S | S | S | S | S | S |
| AL | M | S | M | U | S | S | S | S | S | S |
| Ratawi | M | U | U | U | U | U | U | U | U | — |
| SB | U | U | S | S | S | S | S | S | S | S |
| RG | S | U | U | U | U | U | U | U | U | — |
| Murban | M | S | S | M | S | S | S | S | S | S |
| RJ | U | U | S | U | U | S | U | U | U | — |
| ML | M | S | S | M | S | S | S | S | S | S |
| Erha | U | S | S | S | S | S | S | S | S | S |
| MH | M | S | S | S | S | S | U | S | S | S |
| Antan | M | S | S | M | S | S | S | S | S | S |
| Mascila | M | S | S | U | S | S | U | S | U | S |
| Kuwaity | M | M | U | U | U | S | S | M | S | S |
| AM | M | S | M | U | U | S | S | S | S | S |
| NB | M | S | S | M | S | S | U | S | U | — |

CII (Colloidal Instability Index); CSI (Colloidal Stability Index); SI (stability index); QQA (qualitative-quantitative analysis); SP (Stankiewics plot); SCP (Stability Cross Plot); Unstable (U), Stable (S), Metastable (M).

Among all these, SARA based six different methods, SCP and SP method observed to be closer with K model prediction. The maximum deviations of K model results were observed with CII method.

Further, HP parameters ($C_{min}$, $FR_{max}$, $P_a$, $P_0$, and P) and OCM parameters ($H_D$, $I_N$, $S_{BN}$, $S_{BN}/I_N$) have been estimated based on Eq. (3) to Eq. (9) as mentioned in examples 2.8 and 2.9 respectively and reported in table 7.

During experiments, it has been noted that HP and OCM method is purely based on visual decision for considering the data for estimating the parameters for both the methods. This does not account for the quantity of asphaltene. Hence, both these correlations may not be useful to predict the asphaltene stability limits in crude oils and compatibility of blends.

TABLE 7

Comparison of K model with Heithaus's parameters (P) and OCM's parameters

| Crude Oil | Heithaus's parameters (HP) | | | | | | K model | OCM's parameters | | | | |
|---|---|---|---|---|---|---|---|---|---|---|---|---|
| | $C_{min}$ | $FR_{max}$ | $P_a$ | $P_0$ | P | HP | K | HD | $I_N$ | $S_{BN}$ | $S_{BN}/I_N$ | OCM |
| AH | 0.76 | 0.32 | 0.68 | 0.74 | 2.32 | S | U | 85.52 | 31.61 | 68.57 | 2.17 | S |
| AEL | 1.42 | 0.37 | 0.63 | 0.63 | 1.70 | S | S | 172.64 | 37.83 | 59.74 | 1.58 | S |
| AL | 1.52 | 0.27 | 0.73 | 0.45 | 1.66 | S | S | 176.38 | 27.30 | 42.78 | 1.57 | S |
| Ratawi | 0.77 | 0.46 | 0.54 | 1.06 | 2.30 | S | U | 86.35 | 47.00 | 101.43 | 2.16 | S |
| SB | 0.79 | 0.05 | 0.95 | 0.11 | 2.27 | S | S | 96.44 | 0.53 | 1.08 | 2.04 | S |
| RG | 0.76 | 5.13 | −4.13 | 11.88 | 2.32 | S | U | 81.38 | 51.65 | 115.12 | 2.23 | S |
| Murban | 1.02 | 0.29 | 0.71 | 0.57 | 1.98 | S | S | 121.94 | 28.52 | 51.91 | 1.82 | S |
| RJ | 0.67 | 0.11 | 0.89 | 0.27 | 2.49 | S | U | 76.62 | 10.78 | 24.85 | 2.31 | S |
| ML | 0.63 | 0.11 | 0.89 | 0.28 | 2.59 | S | S | 77.65 | 11.13 | 25.46 | 2.29 | S |
| Erha | 0.66 | 0.11 | 0.89 | 0.28 | 2.52 | S | S | 76.59 | 11.02 | 25.41 | 2.31 | S |
| MH | 1.36 | 0.25 | 0.75 | 0.43 | 1.74 | S | S | 164.50 | 24.61 | 39.57 | 1.61 | S |
| Antan | 0.70 | 0.08 | 0.92 | 0.19 | 2.43 | S | S | 78.62 | 8.17 | 18.56 | 2.27 | S |
| Mascila | 1.53 | 0.34 | 0.66 | 0.56 | 1.65 | 5 | U | 176.10 | 34.30 | 53.78 | 1.57 | 5 |
| Kuwaity | 0.73 | 0.30 | 0.70 | 0.71 | 2.37 | S | S | 73.65 | 26.00 | 61.30 | 2.36 | S |
| AM | 0.92 | 0.28 | 0.72 | 0.58 | 2.09 | S | S | 105.61 | 27.91 | 54.34 | 1.95 | S |
| NB | 0.69 | 0.15 | 0.85 | 0.37 | 2.45 | S | U | 79.75 | 15.38 | 34.67 | 2.25 | S |

Crude Oils:
AH = Arab Heavy, AEK = Amb Extra Light, AL = Arab Light, SB = Saharan Blend RG = Ras Gharib, RJ = Rajasthan, ML = Marib Light, MH = Mumbai High, AM = Arab Mix, NB = Nile Blend The HP and OCM compatibility results of all sixteen crude oils have been compared with K model. Based on HP and OCM parameters and criteria, it has been observed that all sixteen crude oils are stable. HP and OCM methods are similar in nature and related. It is noted that K model prediction does not agree with both the methods for unstable samples.

Example 6: Optimizing Crude Oil Blends for Increasing Heavy Oil Processing

From table 4, three different heavy oils viz. AH, Ratawi and Ras Gharib which are high in asphaltene content have been identified for optimizing the crude oil blends with light crude oils like AEL, AL, Murban, SB, ML, MH from the same table to increase use of heavy oil in refinery processes.

There were five different constraints posed for optimization of crude oil blends for increasing heavy oil processing as discussed above. These constraints are mainly (i) Compatibility (K>=0), (ii) Kinematic Viscosity (V≤10 cSt @ 40° C.), (iii) Pour point (P≤10° C.), (iv) Sulphur (S≤2.5 wt %) and (v) Vacuum Residue Yield (Y≤20.0 wt %) respectively. These are the operational parameters that need to be maintained within workable ranges depending upon refinery configurations for processing crude oils at refineries.

The K model represented by Eq. 1 has been used for the constraint K while optimizing these blends and the parameters are S, C, V, and API for the K model and the other constraints have been determined for the blend using models known in the art. For P and Y also models known in the art have been used. For example, the models for Y, V and P are mainly based on mathematical combination of the measurement on individual oils in proportion to their weight ratios. As Sulphur is a linear, additive property, when different crude oils are blended in different compositions for optimization, sulphur parameter constraints can be estimated with simple addition rule. By using these models and constraints, optimal blend composition for increasing processing of AH, Ratawi and RG with other oils have been estimated and the results are shown in table 8.

the blends mentioned above. Based on SARA analysis, various compatibility parameters such as CII, CSI, SI, QQA, SP, and SCP results have been estimated for the blends.

Figure 8:
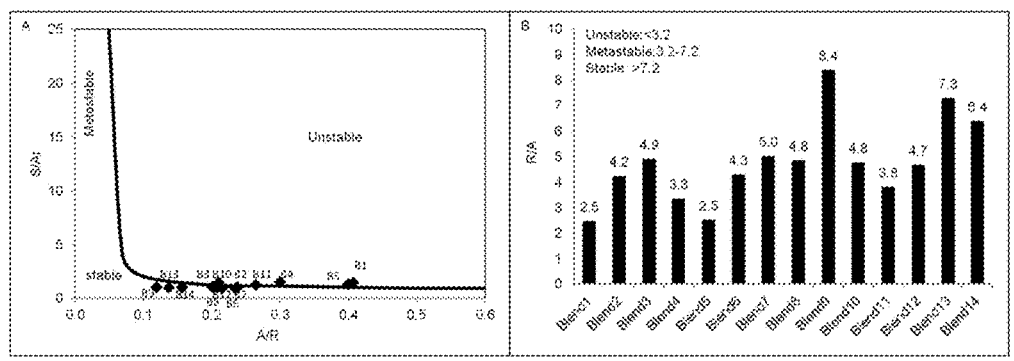
FIG. 8 illustrates Stability criteria: (A) Stankiewicz plot (SP) and (B): Sepulveda chart for crude oil blends, in accordance with an implementation of the present subject matter.
Figure 9:
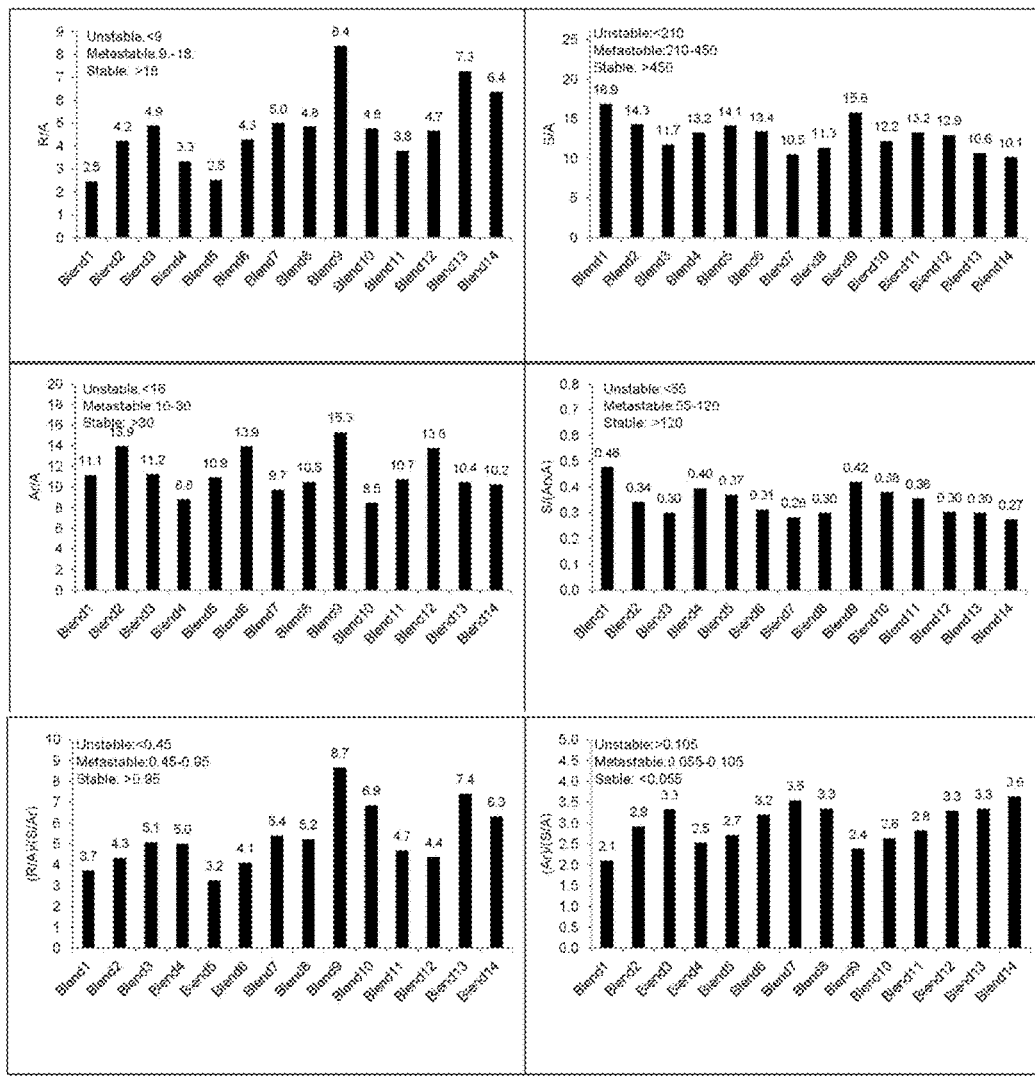
FIG. 9 illustrates Plots of QQA: (i) Resin/Asphaltene; (ii) Saturates/Asphaltene; (iii) Aromatics/Asphaltene; (iv) Saturates/(Aromatics.Asphaltene); (v) (Resin/Asphaltene)/(Saturates/Aromatics); (vi) (Aromatics)/(Saturates/Asphaltene) for crude oil blends, in accordance with an implementation of the present subject matter.
Figure 10:
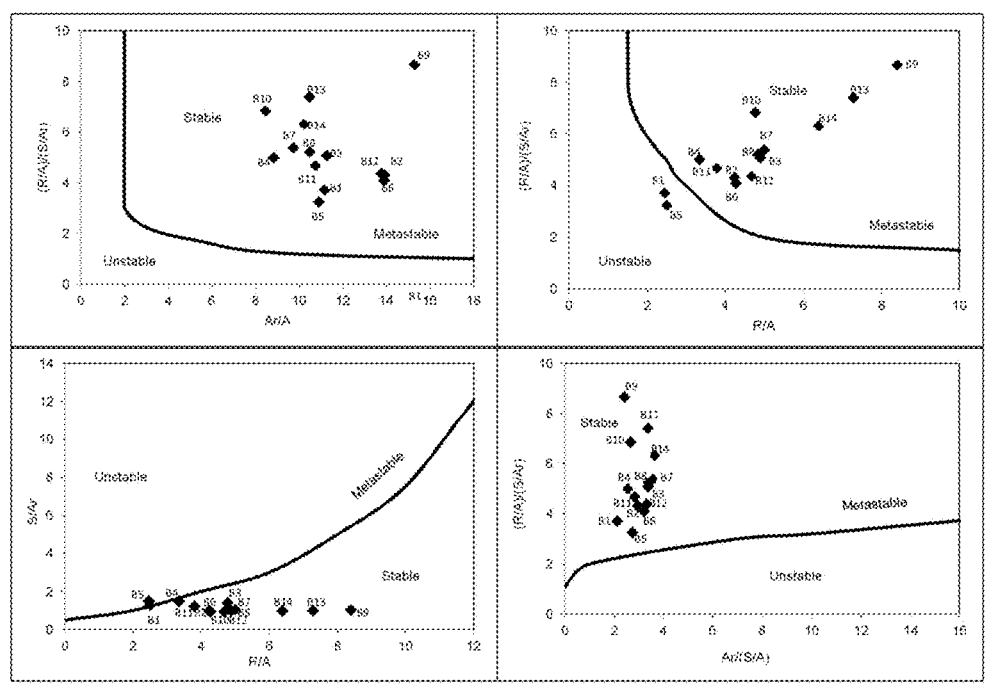
FIG. 10 illustrates Plots of SCP: (i) (Resin/Asphaltene)/(Saturates/Aromatics) vs. Aromatics/Asphaltene; (ii) (Resin/Asphaltene)/(Saturates/Aromatics) vs. Resin/Asphaltene; (iii) Saturates/Aromatics vs. Resin/Asphaltene; (iv) (Resin/Asphaltene)/(Saturates/Aromatics) vs. (Aromatics)/(Saturates/Asphaltenes) for crude oil blends, in accordance with an implementation of the present subject matter.

According to SP plot, prediction of K model is in agreement except three blends viz. blends 1, 4 and 5 blends which were observed to be at metastable line as depicted in FIG. 8. According to Sepulveda chart, most of the blends are not in agreement with K model prediction especially blends 1 and 5. QQA method does not agree with K model prediction even for one blend as observed from FIG. 9 and its criteria. However, K model prediction is in line with composite results of SCP method prediction for all blends as depicted in FIG. 10.

CII prediction results were observed to be not in agreement with K model prediction. However, CSI prediction observed to be in line with K model prediction except for

TABLE 8

Optimized blends for increasing heavy oil processing

| | Crude oils blends | | Compatibility | | Final blend properties for processing | | | | | | | | | |
|---|---|---|---|---|---|---|---|---|---|---|---|---|---|---|
| SN | HO | LO | K | Blends | A | S | V | P | C | Y | Sat | Ar | R | A |
| B1 | AH | AEL | 0.00 | 50/50 | 32.40 | 1.74 | 7.25 | −49 | 5.08 | 20.00 | 53.60 | 35.42 | 7.81 | 3.18 |
| B2 | AH | AL | 0.00 | 30/70 | 31.29 | 1.98 | 8.04 | −51 | 5.69 | 21.76 | 44.75 | 41.37 | 12.55 | 3.63 |
| B3 | Ratawi | Murban | 0.00 | 51/49 | 30.76 | 2.42 | 9.33 | −22 | 6.04 | 22.75 | 39.67 | 39.56 | 16.49 | 4.28 |
| B4 | Ratawi | SB | 0.00 | 53/47 | 30.27 | 2.50 | 9.53 | −24 | 6.09 | 23.06 | 48.48 | 34.42 | 12.85 | 4.25 |
| B5 | Ratawi | AEL | 0.00 | 53/47 | 30.27 | 2.50 | 9.53 | −24 | 6.09 | 23.06 | 46.66 | 39.00 | 9.95 | 4.39 |
| B6 | Ratawi | AL | 0.00 | 31/69 | 30.13 | 2.41 | 9.31 | −31 | 6.22 | 23.35 | 39.84 | 42.58 | 13.43 | 4.15 |
| B7 | Ratawi | ML | 0.00 | 63/37 | 30.82 | 2.50 | 9.72 | −20 | 6.75 | 24.24 | 38.68 | 38.59 | 17.69 | 5.04 |
| B8 | Ratawi | MH | 0.00 | 62/38 | 30.02 | 2.45 | 9.47 | 1 | 6.65 | 24.33 | 39.32 | 39.17 | 16.57 | 4.93 |
| B9 | RG | Murban | 0.00 | 24/76 | 33.99 | 1.50 | 6.17 | −14 | 3.91 | 16.32 | 39.07 | 37.77 | 20.70 | 2.47 |
| B10 | RG | SB | 0.00 | 47/53 | 33.44 | 32.62 | 1.71 | 7 | −4.99 | 5.51 | 21.08 | 32.62 | 18.71 | 4.13 |
| B11 | RG | AEL | 0.00 | 26/74 | 33.12 | 1.63 | 6.48 | −14 | 4.03 | 16.75 | 49.92 | 36.79 | 10.70 | 2.58 |
| B12 | RG | AL | 0.00 | 15/85 | 31.19 | 2.02 | 8.05 | −22 | 5.41 | 21.05 | 39.04 | 42.44 | 15.12 | 3.40 |
| B13 | RG | ML | 0.00 | 38/62 | 34.57 | 1.40 | 6.33 | −7 | 4.68 | 18.65 | 36.24 | 35.58 | 24.77 | 3.41 |
| B14 | RG | MH | 0.00 | 36/64 | 33.24 | 1.34 | 6.04 | 10 | 4.52 | 18.68 | 37.60 | 36.57 | 22.65 | 3.18 |

HO = Heavy Oils, LO = Light oils, K = Compatibility, A = API, S = Sulphur, V = Kinematic Viscosity, P = Pour Point, C = MCCR, Y = VR Yield, Sat = Saturates, Ar = Aromatics, R = Resins, Asph = Asphaltene Other physico-chemical characterization data including SARA analysis has also been experimentally measured for blend 1. All these different compatibility results have been compared with K model and presented in table 9.

TABLE 9

Validation of K model with results obtained with different methods for blends

| | Crude oils blends | | | | Compatibility | | | | | | | | | |
|---|---|---|---|---|---|---|---|---|---|---|---|---|---|---|
| SN | HO | LO | K | Stable blends | CII | CSI | SI | QQA | SP | SCP | Spot Test | Composite Result | K Model | Refinery Experience |
| SN | AH | AEL | 0.00 | 50/50 | U | S | U | U | M | S | S | M | S | S |
| B1 | AH | AL | 0.00 | 30/70 | M | S | S | U | S | S | S | S | S | S |
| B2 | Ratawi | Murban | 0.00 | 51/49 | M | S | S | U | S | S | S | S | S | — |
| B3 | Ratawi | SB | 0.00 | 53/47 | U | S | S | U | M | S | S | S | S | — |
| B4 | Ratawi | AEL | 0.00 | 53/47 | U | S | U | U | S | S | S | S | S | — |
| B5 | Ratawi | AL | 0.00 | 31/69 | M | S | S | U | S | S | S | S | S | — |
| B6 | Ratawi | ML | 0.00 | 63/37 | M | S | S | U | S | S | S | S | S | — |
| B7 | Ratawi | MH | 0.00 | 62/38 | M | S | S | U | S | S | S | S | S | — |
| B8 | RG | Murban | 0.00 | 24/76 | M | S | S | U | S | S | U | S | S | — |
| B9 | RG | SB | 0.00 | 47/53 | U | S | S | U | S | S | S | S | S | — |
| B10 | RG | AEL | 0.00 | 26/74 | M | S | S | U | S | S | M | S | S | — |
| B11 | RG | AL | 0.00 | 15/85 | M | S | S | U | S | S | S | S | S | — |

TABLE 9-continued

Validation of K model with results obtained with different methods for blends

| Crude oils blends | | | | Compatibility | | | | | | | | | |
|---|---|---|---|---|---|---|---|---|---|---|---|---|---|
| SN | HO | LO | K | Stable blends | CII | CSI | SI | QQA | SP | SCP | Spot Test | Composite Result | K Model | Refinery Experience |
| B12 | RG | ML | 0.00 | 38/62 | S | S | S | U | S | S | S | S | S | — |
| B13 | RG | MH | 0.00 | 36/64 | S | S | S | U | S | S | S | S | S | — |

HO = Heavy Oils, LO = Light oils, K = Compatibility, CII (Colloidal Instability Index); CSI (Colloidal Stability Index); SI (stability index); QQA (qualitative-quantitative analysis); SP (Stankiewics plot); SCP (Stability Cross Plot);

Refinery experience indicates the actual behaviour of the blend when tried in a refinery. AH with AEL and AH with AL blends were tried in refineries and these results were observed to be in line with K model prediction as presented in table 9.

Figure 11A:
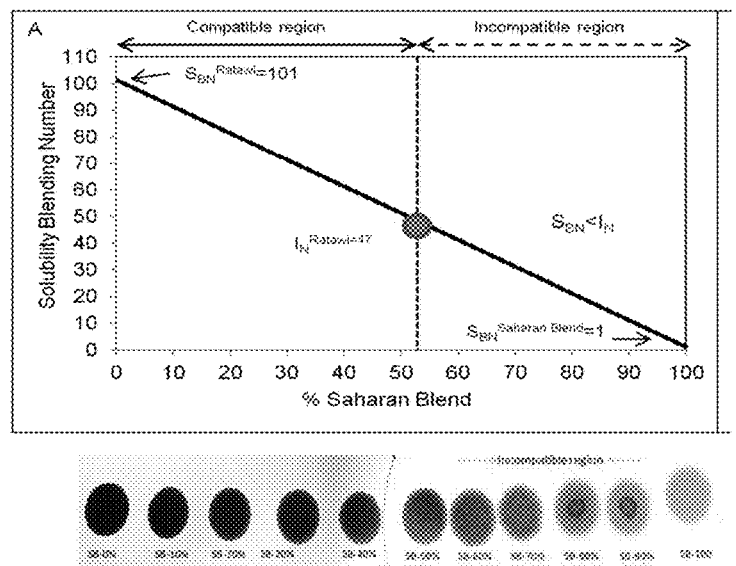
FIG. 11A illustrates estimation of compatible blends of Ratawi and Saharan Blend using OCM method, in accordance with an implementation of the present subject matter.
Figure 11B:
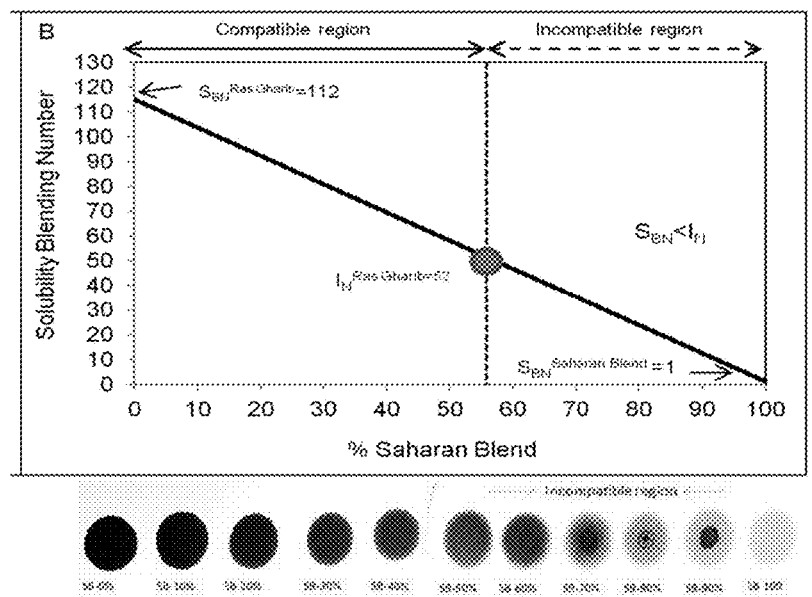
FIG. 11B illustrates estimation of compatible blends of Ras Gharib and Saharan Blend using OCM method, in accordance with an implementation of the present subject matter.

Further, in the present case, two blends (i) Ratawi with SB (blend 4) and (ii) RG with SB (blend 10) have been analysed using $S_{BN}$ and $I_N$ values from table 7. These values were used to estimate the compatible composition for these blends as depicted in FIG. 11 A and FIG. 11 B respectively. It has been observed that compatible composition for these two blends (blends 4, 10) were Ratawi:SB=53:47 and RG:SB=56:44, respectively. The OCM results observed to be in line with K model prediction. Also, the spot tests results for these blends (blends 4, 10) are in line with K model. However, this particular OCM method may not be used for all combination of heavy and light crude oils. This required $I_N$ value of one of the two crude oils to be in between $S_{BN}$ numbers of crude oils to be blended otherwise, this method may not be fit to estimate the compatible blend composition. For example, the estimation of compatible composition of AH (68.57, 31.61) with AEL (59.74, 37.83) or AL (42.78, 27.30) is not possible as $I_N$ values of any crude oils does not fall in between the $S_{BN}$ values of the crude oils to be blended. In such scenario, K model will be helpful to estimate the compatible blend composition for increasing heavy oil processing.

Example 7: Prediction of Intensity of Spot Test Shades

Figure 12:
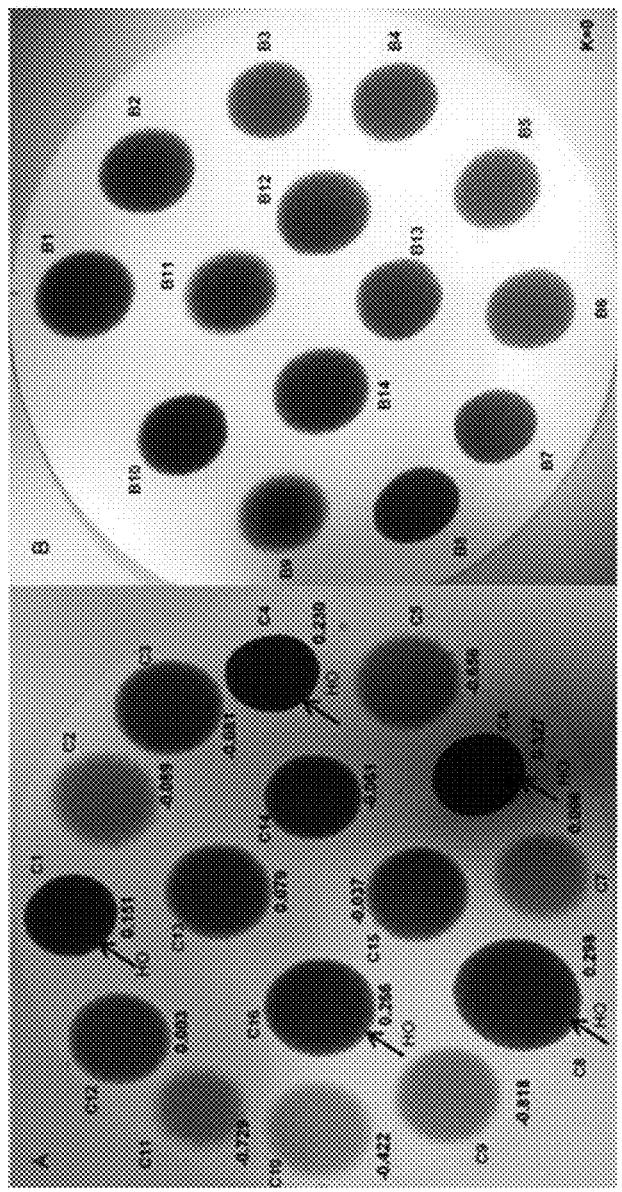
FIG. 12 illustrates Prediction of intensity of spot test shades: (A) To distinguish between light and heavy crude oils and (B) compatible crude oil blends using K value, in accordance with an implementation of the present subject matter.

Spot tests of sixteen crude oils (table 4) and fourteen crude oil blends (table 8) have been carried out as per ASTM D4740 as depicted in FIGS. 12A and B respectively. FIG. 12A is the spot test of neat crude oils. K value of these neat crude oils have been predicted and shown near the spots. It has been noted that higher K value results in high intensity of the shades i.e., dark in colour and they are heavy oils irrespective of whether they are with high asphaltenes or less asphaltenic crude oils. For example, the Arab Heavy (K=0.151) Ratawi (K=0.230) and Ras Gharib (K=0.327) crude oils have high asphaltene content and Rajasthan (K=0.298), Nile Blend (K=0.266) are paraffinic crude oils. All these crude oils are observed with dark black in shades. Similarly, lower K value indicated about light crude oils. The K value can further be used to classify the intensity shades of spot tests and helpful in identifying the extent of heavy and light crude oils. For example, a regression can be carried out between the K value and intensity of the spot as measured by, for example, a spectrophotometer and the K value can be used to predict the intensity.

Similarly, the spots were analyzed for optimal blends of crude oils (table 8). From FIG. 12B, this showed the prediction of K value and indication about the stability of the samples. Here, it has been noted that optimal blends shades are in balanced color, i.e., they are neither too dark nor too light. Blends have been optimized for K value ≥zero. Hence, even for blends, the K value can be used to predict the intensity of the spot obtained in a spot test. Since a spot test can involve human error due to difference in application of spot, dilution, etc., the prediction of intensity using K value is more reliable.

Example 8: Desalting Performance of Oil Blends Selected Based on K Model

K model predicted incompatible blend A (Ras Gharib 35 wt % and Saharan Blend 65 wt %, having K<0) and compatible blend B (Ras Gharib 65 wt % and Saharan Blend 35 wt %, having K>0) were subjected to desalting experiments. In desalting experiments, water separation efficiency is the main performance parameter tested. Water is used for removal of salt in refinery operations. However, while using water and vigorous mixing, emulsion forms. Separation of water after the emulsion formation is important for desalting and for this demulsifier chemicals are being used in refinery.

For the desalting experiment, a 5% by vol water was added to both the crude blends A and B and stirred in such a way that water does not get separated, for 45 minutes. 75 ml of the emulsion was transferred to Portable Electrostatic Desalter (PED) tubes. Both the tubes were placed in the PED and heated to 80° C. and checked for water separation. The tubes were then heated to 110-120° C. Same weight by ppm of the demulsifier to the crude blends was added to each of the tubes. Each tube was given 100 shakes for proper mixing. Millimeters of water separated at each tube recorded as zero-minute reading, before voltage is applied. Tubes kept under electrical voltage of 3 kV, at 110-120° C. and water separation in mm recorded after 5 & 10 minutes' exposure. Water separated for all the samples were recorded. Interface layer between water and crude was clear, without any intermediate layer.

Figure 13:
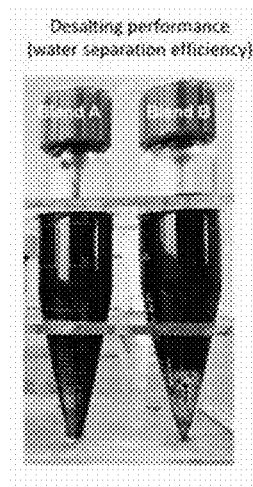
FIG. 13 illustrates comparative results of desalting experiments on compatible and incompatible blends, in accordance with an implementation of the present subject matter.

Dehydration efficiency was calculated as the ratio of separated water to the added water after 5 and 10 minutes. The Dehydration efficiency (water separation) is estimated as 37.78 wt % and 41.12 wt % for 5 and 10 minutes respectively with compatible blend B however, there is no water separation observed with incompatible blends as shown in FIG. 13. In this case, this experimental result is the evidence of strong relationship between K model and desalting performance. Therefore, the optimization of blends using K model can be further used for optimizing demulsifier chemical dosing for improving desalting efficiency.

Example 9: Fouling Performance of Oil Blends Selected Based on K Model

K model predicted incompatible blend A (Ras Gharib 35 wt % and Saharan Blend 65 wt %, having K<0) and compatible blend B (Ras Gharib 65 wt % and Saharan Blend 35 wt %, having K>0) were subjected to fouling thermal experiments. In fouling, thermal experiments, temperature drop profile is the main performance parameter tested.

For the fouling thermal experiment, a Thermal Fouling Tester (FT2) is used to find the fouling propensity of refinery streams. The results of this study are not absolute as the experiments are simulating accelerated fouling conditions. However, this test is very useful to compare the fouling behavior of various refinery streams.

In this experiment, a rod is electrically heated and crude oil blends A and B flowed around the heating rod in the annular space. This heating rod is used to heat up these samples flowing around it. The temperature of the rod (Ts) and the inlet temperature (Tin) of the samples were kept constant so that Ts>Tin.

The heat transfer took place between the heated rod and the samples A and B. The outlet of crude oil blend A and B were received at higher temperature (Tout). Hence, the relative temperatures are: Ts>Tout>Tin.

Figure 14:
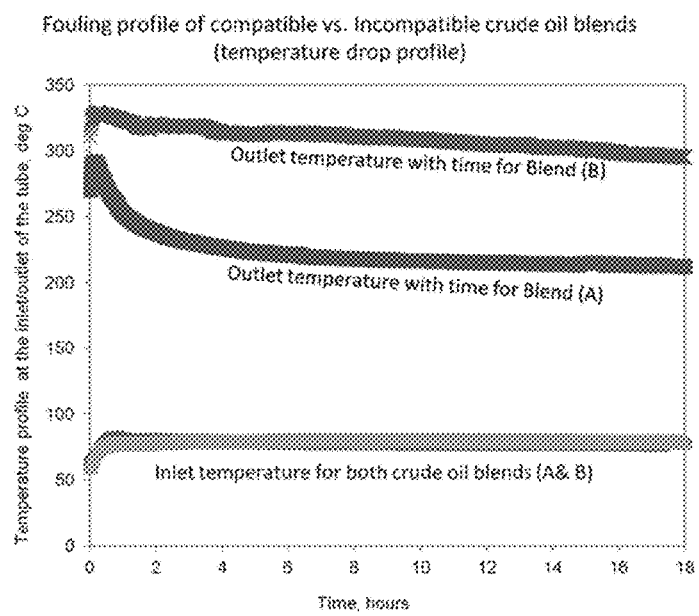
FIG. 14 illustrates comparative results of fouling experiments on compatible and incompatible blends, in accordance with an implementation of the present subject matter.

As per FIG. 14, it is noted that in case of compatible blends the temperature drop is about 34° C., however, incompatible blends observed with very high temperature drop of about 80° C. This clearly showed that deposition in incompatible blend A is higher as compared to compatible blend B over the surface of heating rod and the heat transfer rate reduced significantly. In this case, this experimental result is the evidence of strong relationship between K model and fouling profile. Thus, the optimization of blends using K model can be further used for optimizing antifouling chemical dosing for fouling mitigation.

Summary of Validation Results

As the prior art methods, individually, have been unsatisfactory for compatibility results, K model has been validated with the composite results of the different compatibility tests available in the literature for accurate prediction of compatibility/stability. K model predictions have been more close to SCP, SP and spot test methods and maximum deviation from CII prediction in individual comparison. HP and OCM methods were found to be unsatisfactory with K model for crude oils. OCM was found to have a limitation especially when IN value of one of the two crude oils are not in between SBN numbers of crude oils to be blended for estimating compatible blend composition. K model has been separately validated for neat crude oils and heavy/light crude oil blends and found accurate in prediction.

The use of the K model for compatibility prediction and optimization has a number of advantages. For example, the prediction of K value is based on measurement of physical parameter ratios (API/S, S/V, C/API, C/S, V/API, V/C etc.). The K model does not require different comprehensive laboratory experiments for prediction of compatibility of crude oils and blends. The K model is generic in nature in its applicability for predicting compatibility. This can be used for predicting compatibility a blend of multiple crude oils as this is based on physical parameter ratios. The K model is also helpful in optimizing crude oil blend compositions wherein heavy oil processing can be safely increased without compatibility related problems with meeting other processing and operational requirements at refineries.

Furthermore, the K model is able to predict the shades of light to heavy crude oils as the shades correspond to variation of K value from low to high. According to K value, the intensity of spot test shade changes and in turns the type of crude oils (light and heavy). Higher K indicates dark color and lower value indicates light color.

Based on the teachings of the present disclosure, a testing apparatus can also be developed for determination of different physical properties of a crude oil sample and for providing the determined properties to a system, such as the system 100 for determining the crude oil blend compatibility.

Figure 15:
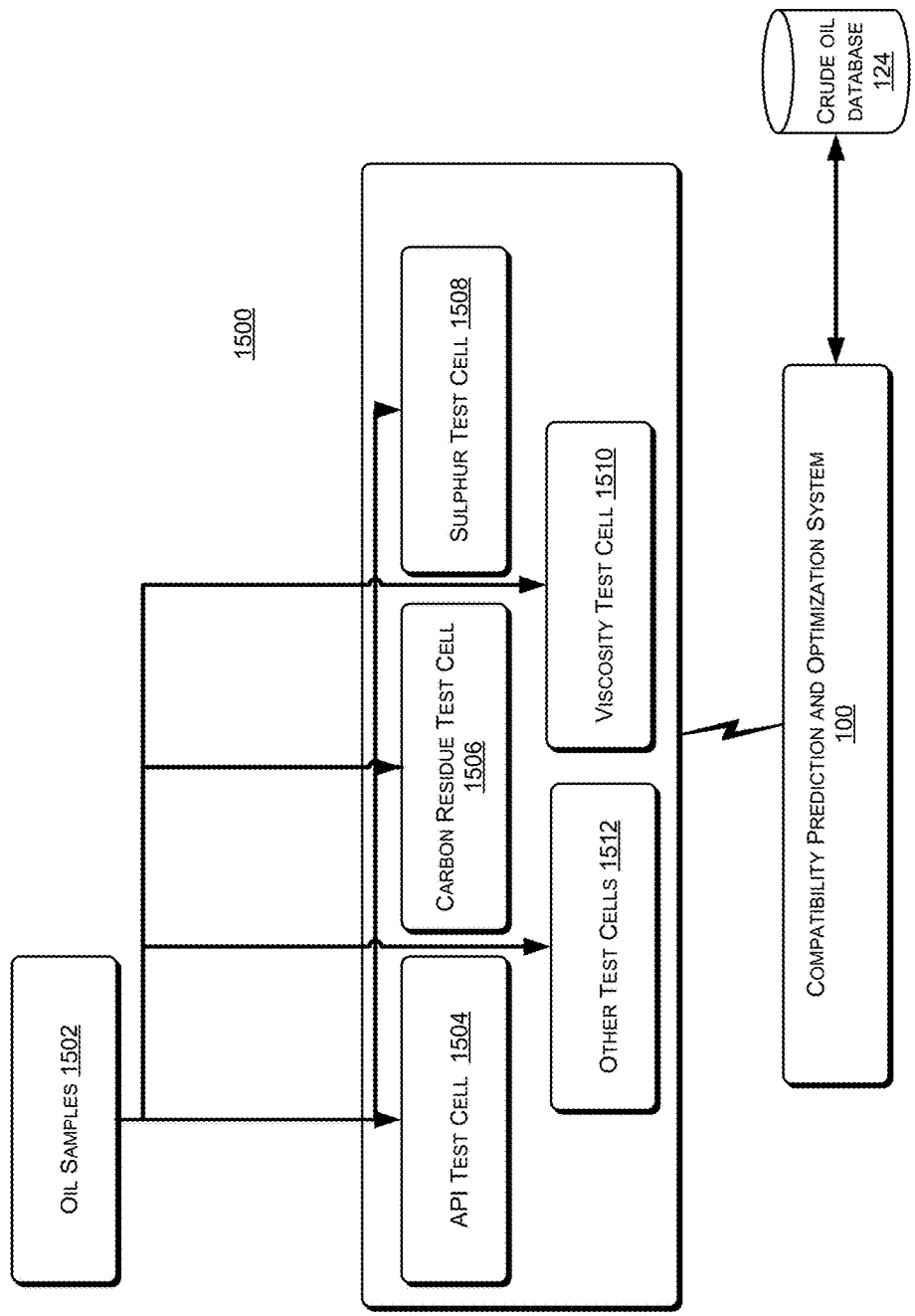
FIG. 15 illustrates an apparatus for estimation of crude oil blend compatibility based on measurement of physical parameter ratios, in accordance with an implementation of the present subject matter.

FIG. 15 illustrates a computing network comprising an example apparatus 1500 for testing crude oil samples 1502 for determination of different physical properties of the oil samples 1502. The apparatus 1500 is in communication with the system 100 for predicting the compatibility of the oil samples and optimizing an oil blend comprising at least one heavy oil from the oil samples.

In one example, the apparatus 1500 may comprise a plurality of test cells, for example, an API test cell 1504, a CCR test cell 1506, a Sulphur test cell 1508, a Viscosity test cell 1510. Further, the apparatus may also comprise other test cell(s) 1512. The apparatus 1500 may be coupled to the system 100 in order that the system 100 may receive the determined values of the physical properties of the crude oil samples 1502 for the prediction of compatibility of the crude oils in crude oil blends and for optimizing the blend ratios.

In operation, the crude oil samples 1502 are fed into the apparatus 1500 for determining the physical parameters. The crude oil samples 1502 may be channelized into the apparatus 1500 to ensure that the crude oil samples 1502 are individually fed into each test cell or the specific test cells selected by a user.

The API test cell 1504 is configured to test the oil samples for determination of the API gravity of each of the crude oil samples 1502. The API test cell may be further configured to store the determined value of the API gravity of the crude oil samples 1502 in order to provide the value of API gravity to the system 100. Similarly, the CCR test cell 1506 may be configured to determine and store the value of CCR content of the crude oil samples 1502. Further, the Sulphur test cell 1508 may be configured to determine and store the value of Sulphur content of the crude oil samples 1502 and the Viscosity test cell 1510 may be configured to determine and store the value of Kinematic Viscosity of the crude oil samples 1502. This can be done for each crude oil to be used in the blend.

Thus, the apparatus 1500 may be used in a laboratory for performing the tests on the crude oil samples 1502 for measurement of physical properties in order to predict the compatibility of the crude oil samples 1502. Furthermore, the other test cell(s) 1510 may be configured to determine and store the value of other physical parameters of the crude oil samples 1502, such as Carbon content, Hydrogen content, Paraffins, Basic Nitrogen content, Total Nitrogen content, Mercaptan, Pour point, Saturates, Aromatics, Resins, and Asphaltenes, and the like.

Based on the determined properties, the compatibility of the crude oils, their blends, and optimized blends can be determined using the models as discussed herein.

Although implementations for prediction of compatibility of crude oil blends have been described in language specific to structural features and/or methods, it is to be understood that the appended claims are not necessarily limited to the specific features or methods described. Rather, the specific features and methods are disclosed as example implementations for prediction of compatibility of crude oil blends.

We claim:

1. A method for predicting compatibility of unknown crude oils and optimizing crude oil blend for increasing heavy oil processing in refineries, the method comprising:

receiving values for a plurality of physical parameter ratios of unknown crude oil samples, wherein the physical parameter ratios are based on parameters selected from Kinematic Viscosity (V), Sulphur (S), Carbon Residue (C), and American Petroleum Institute (API) gravity;

predicting the compatibility for each unknown crude oil sample based on a compatibility prediction model by using the received values as an input to the compatibility prediction model, wherein the compatibility prediction model is to predict a compatibility parameter (K) for the unknown crude oil samples based on coefficients of regression obtained from correlating the physical parameter ratios for known crude oils with respective composite compatibility measures, the composite compatibility measures being a composite of results obtained from a plurality of compatibility that are based on compositions of the known crude oils, wherein the plurality of compatibility tests are selected from colloidal instability index (CII), colloidal stability index (CSI), Stability Index (SI), Stankiewicz plot (SP), qualitative-qualitative analysis (QQA), stability cross plot (SCP), Heithaus parameter (or parameter P), toluene equivalence (TE) test, Heptane dilution (HD) test, and oil compatibility model (OCM); and determining an optimized blend for refinery processing, the optimized blend comprising at least one heavy oil from the unknown crude oils and one or more other crude oils, wherein the optimized blend is determined based on a multi-objective optimization model comprising a constraint on the compatibility parameter (K) of the optimized blend as an objective.

2. The method as claimed in claim 1, wherein the unknown crude oils are at least one of a crude oil, synthetic crude oil, a refinery product stream, an unknown hydrocarbon mixture, and a combination thereof.

3. The method as claimed in claim 1, wherein the plurality of physical parameter ratios includes at least API/S, V/C, and log(S)/C.

4. The method as claimed in claim 1, wherein the coefficients of regression are calculated based on one of linear regression and non-linear regression.

5. The method as claimed in claim 1, wherein determining the optimized blend comprises optimizing weight ratios of the at least one heavy oil and the one or more other crude oils based on constraints placed on K value determined by the compatibility prediction model, Kinematic Viscosity, Pour point, Vacuum residue yields, and Sulphur content.

6. The method as claimed in claim 1, wherein a composite compatibility measure for a crude oil is based on at least six compatibility tests.

7. The method as claimed in claim 1, wherein the compatibility is negatively correlated to Log (Sulphur)/Carbon Residue, Carbon Residue/Sulphur, Carbon Residue/API, API/Sulphur, Kinematic Viscosity/API, and 1/Carbon Residue.

8. The method as claimed in claim 1, wherein the compatibility is positively correlated to Sulphur/Kinematic Viscosity and Kinematic Viscosity/Carbon Residue.

9. The method as claimed in claim 1, wherein the compatibility predicted by the compatibility prediction model is positively correlated to intensity of spot obtained in a spot test.

10. The method as claimed in claim 1, wherein the at least one heavy oil is selected from the unknown crude oils for blending based on the predicted compatibility.

11. The method as claimed in claim 1, wherein the optimized blend has lower fouling tendency and lower temperature drop than incompatible blends.

12. The method as claimed in claim 1, wherein the optimized blend has better desalting efficiency and better water separation efficiency than incompatible blends.

13. A system for predicting compatibility of unknown crude oils and optimizing crude oil blend for increasing heavy oil processing in refineries, the system comprising:
a processor;
an interface; and
a memory coupled to the processor, the memory comprising:
a receiving module configured to receive values of a plurality of physical parameter ratios based on Kinematic Viscosity (V), Sulphur (S), Carbon Residue (C), and American Petroleum Institute (API) gravity for unknown crude oil samples;
a regression module configured to compute coefficients of regression for a compatibility prediction model, wherein the compatibility prediction model is to predict a compatibility parameter (K) for unknown crude oil samples based on the plurality of physical parameter ratios and the coefficients of regression, the coefficients of regression being obtained from correlating the physical parameter ratios for known crude oils with respective composite compatibility measures, the composite compatibility measures being a composite of results obtained from a plurality of compatibility tests that are based on compositions of the known crude oils, wherein the plurality of compatibility tests are selected from colloidal instability index (CII), colloidal stability index (CSI), Stability Index (SI), Stankiewicz plot (SP), qualitative-qualitative analysis (QQA), stability cross plot (SCP), Heithaus parameter (or parameter P), toluene equivalence (TE) test, Heptane dilution (HD) test, and oil compatibility model (OCM);
a prediction module configured to predict the compatibility for each unknown crude oil sample based on the compatibility prediction model by using the received values as an input to the compatibility prediction model; and
an optimization module configured to determine an optimized blend for refinery processing, the optimized blend comprising at least one heavy oil from the unknown crude oils and one or more other crude oils, wherein the optimized blend is determined based on a multi-objective optimization model comprising a constraint on the compatibility parameter (K) of the optimized blend as an objective.

14. The system as claimed in claim 13, wherein the unknown crude oil is a refinery product stream and wherein the optimization module is configured to determine the optimized blend of the unknown crude oil with the one or more other crude oils, wherein the refinery product stream includes at least one of clarified oil, bitumen, vacuum residue, long residue, light cycle oil heavy cycle oil, vacuum gas oil, kerosene, diesel, Gas oil, atmospheric residue, Fuel Oil, Low Sulphur Heavy Stock, unconverted oils, bottom residue and their unknown blends.

15. The system as claimed in claim 13, wherein the unknown crude oils are selected from a crude oil, synthetic crude oil, unknown hydrocarbon mixture, and a combination thereof.

16. The system as claimed in claim 13, wherein the plurality of physical parameter ratios includes at least A/S, V/C, and log(S)/C.

17. The system as claimed in claim 13, wherein the compatibility is negatively correlated to Log (Sulphur)/Carbon Residue, Carbon Residue/Sulphur, Carbon Residue/API, API/Sulphur, Kinematic Viscosity/API, and 1/Carbon Residue.

18. The system as claimed in claim 13, wherein the compatibility is positively correlated to Sulphur/Kinematic Viscosity and Kinematic Viscosity/Carbon Residue.

19. The system as claimed in claim 13, wherein the at least one heavy oil is selected from the unknown crude oils based on the predicted compatibility.

20. The system as claimed in claim 13, wherein the optimization module is to determine the optimized blend by optimizing weight ratios of the at least one heavy oil and the one or more other crude oils based on constraints placed on K value determined by the compatibility prediction model, Kinematic Viscosity, Pour point, Vacuum residue yields, and Sulphur content.

21. A computing network comprising an apparatus for testing unknown crude oil samples for predicting compatibility of unknown crude oils and optimizing crude oil blend for increasing heavy oil processing in refineries, the apparatus comprising:
- an API test cell configured to test the oil samples for determining API gravity of the oil samples;
- a Carbon Residue test cell configured to test the oil samples for determining carbon residue content of the oil samples;
- a Sulphur test cell configured to test the oil samples for determining Sulphur content of the oil samples; and
- a Kinematic Viscosity test cell configured to test the oil samples for determining Kinematic Viscosity of the oil samples;

wherein the computing network further comprises a system for predicting the compatibility of the oil samples and optimizing an oil blend comprising at least one heavy oil from the oil samples, and wherein the apparatus is configured to provide the Kinematic Viscosity, API gravity, the Carbon Residue content, and the Sulphur content of the oil samples to the system; and wherein the system is to
- predict the compatibility for each unknown crude oil sample based on a compatibility prediction model by using the received values as an input to the compatibility prediction model, wherein the compatibility prediction model is to predict a compatibility parameter (K) for unknown crude oil samples based on a plurality of physical parameter ratios and coefficients of regression, the coefficients of regression being obtained from correlating the physical parameter ratios for known crude oils with respective composite compatibility measures, the plurality of physical parameter ratios being based on Kinematic Viscosity (V), Sulphur (S), Carbon Residue (C), and American Petroleum Institute (API) gravity, the composite compatibility measures being a composite of results obtained from a plurality of compatibility tests that are based on compositions of the known crude oils, wherein the plurality of compatibility tests are selected from colloidal instability index (CII), colloidal stability index (CSI), Stability Index (SI), Stankiewicz plot (SP), qualitative-qualitative analysis (QQA), stability cross plot (SCP), Heithaus parameter (or parameter P), toluene equivalence (TE) test, Heptane dilution (HD) test, and oil compatibility model (OCM); and
- determine the optimized oil blend for refinery processing by optimizing weight ratios of the at least one heavy oil and the one or more other crude oils based on a multi-objective optimization model comprising a constraint placed on the compatibility parameter (K) of the optimized blend determined by the compatibility prediction model, and on Kinematic Viscosity, Pour point, Vacuum residue yields, and Sulphur content.

22. The computing network as claimed in claim 21, wherein the apparatus further comprises other test cells configured to test the oil samples to determine at least one of Hydrogen content, Nitrogen content, Mercaptan, Pour point, Ramsbottom Carbon Residue distillation and residue yields, Saturates, Aromatics, Resins, and Asphaltenes of the oil samples.

* * * * *